(12) United States Patent
Lampropoulos et al.

(10) Patent No.: US 7,753,203 B2
(45) Date of Patent: Jul. 13, 2010

(54) SHARPS HANDLING DEVICES

(75) Inventors: Fred P. Lampropoulos, Salt Lake City, UT (US); Gregory R. McArthur, Sandy, UT (US); Jim Mottola, Salt Lake City, UT (US); Anne-Marie Wright, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 12/201,542

(22) Filed: Aug. 29, 2008

(65) Prior Publication Data

US 2010/0051491 A1   Mar. 4, 2010

(51) Int. Cl.
*B65D 83/10* (2006.01)
(52) U.S. Cl. .................................. 206/366; 206/382
(58) Field of Classification Search .............. 206/365, 206/366, 45.2, 45.23, 45.24, 380, 382
See application file for complete search history.

(56) References Cited

U.S. PATENT DOCUMENTS

| | | | | |
|---|---|---|---|---|
| 776,402 A | * | 11/1904 | Johnson | 206/366 |
| 1,960,073 A | * | 5/1934 | Warner | 206/759 |
| 2,962,155 A | * | 11/1960 | Rusciano | 206/365 |
| 4,936,449 A | * | 6/1990 | Conard et al. | 206/366 |
| 4,938,354 A | | 7/1990 | Hernandez | |
| 5,024,326 A | * | 6/1991 | Sandel et al. | 206/366 |
| 5,133,454 A | * | 7/1992 | Hammer | 206/364 |
| 5,372,249 A | * | 12/1994 | Grange | 206/45.23 |
| 5,732,820 A | * | 3/1998 | Tsai | 206/369 |
| 5,967,317 A | * | 10/1999 | Wright | 206/366 |
| 6,581,774 B1 | * | 6/2003 | Galafassi et al. | 206/553 |
| 6,681,925 B2 | * | 1/2004 | Fischer et al. | 206/63.5 |
| 6,886,689 B2 | * | 5/2005 | Hohns et al. | 206/308.3 |
| 6,905,015 B2 | * | 6/2005 | Hernandez et al. | 206/45.24 |
| 2007/0119740 A1 | | 5/2007 | Clegg | |

* cited by examiner

*Primary Examiner*—Jacob K Ackun, Jr.
(74) *Attorney, Agent, or Firm*—Stoel Rives LLP

(57) ABSTRACT

A sharps handling device can include a base and a holder. The base and the holder can form a stand in which sharps devices can be retained so as to be accessible. The base and the holder can also form a container for enclosing sharps devices.

28 Claims, 17 Drawing Sheets

SHARPS HANDLING DEVICES

BACKGROUND

1. Field of the Invention

The present disclosure relates to stands and containers configured for use with sharp medical instruments. More particularly, the present disclosure relates to stands for holding sharps during medical procedures and relates to containers for safe disposal of the sharps thereafter.

2. Relevant Technology

The potential for transmitting illnesses from bodily fluids of patients to practitioners is of great concern in the medical community. Accordingly, safety procedures and regulations have been developed for the periods before, during, and after medical procedures that involve contact with the bodily fluids of a patient. For example, special protocols are recommended and/or required for handling medical apparatus that have contacted bodily fluids and for the disposal of such medical apparatus.

Sharps can pose a significant risk for transmitting blood-borne illnesses, or illnesses from other bodily fluids, due to their ability to penetrate the skin. The term "sharps" is used herein in its ordinary sense and can include items commonly referred to as "surgical sharps" and "sharps instruments," as well as any other instrument or device that poses a risk of contaminating an individual by cutting, puncturing, or otherwise penetrating the individual's skin. Sharps can include, but are not limited to, needles, trocars, scalpels, and other implements with points, edges, or other surfaces that can penetrate the skin.

A number of devices have been developed to protect against accidental cuts or punctures from sharps. For example, holders have been designed to temporarily shield sharp points or edges of an instrument between uses of the instrument over the course of a medical procedure. Additionally, specialized containers for receiving and holding used sharps have been developed to provide for safe and simple disposal of the sharps. Certain policies and regulations for the handling and disposal of sharps have also been implemented to make the advantages rendered by such holders and containers more widespread. For example, some regulations require sharps to be discarded in a certified sharps container that cannot be reopened without significant effort or that is otherwise sealed shut to prevent the container from releasing its contents.

Existing sharps holders can suffer from a variety of shortcomings. For example, traditional sharps holders do not provide a mechanism for safely securing sharps for disposal. The holders are generally designed for use as temporary storage devices and do not function properly for purposes of disposing sharps. Proper disposal of sharps that have been inserted into a temporary holder generally can require transfer of the sharps to a separate disposal container, which can be time consuming and can introduce the possibility of practitioner injury if the sharps implement is not handled carefully.

Additionally, existing sharps holders can provide inadequate support for the weight of sharps instruments that they bear. Consequently, the sharps holders are prone to tipping over. Such tipping can cause syringes or other devices stored in the holders to scatter and, in some cases, to break under their own weight.

A further shortcoming of existing sharps holders is that many existing sharp holders provide a fairly small insertion area or areas. During medical procedures, practitioners are often under time and mental constraints, such that focusing on a small target insertion area in which to insert the sharps device can be disadvantageously time consuming and distracting.

SUMMARY

Certain embodiments of a sharps handling device include a base and a holder. In some embodiments, the base is configured to support the holder in a stand configuration in which the holder can retain sharps devices that are inserted therein in a substantially upright orientation. In further embodiments, the base is configured to couple with the holder in a container configuration in which the base and the holder substantially encase one or more sharps devices that have been inserted in the holder.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
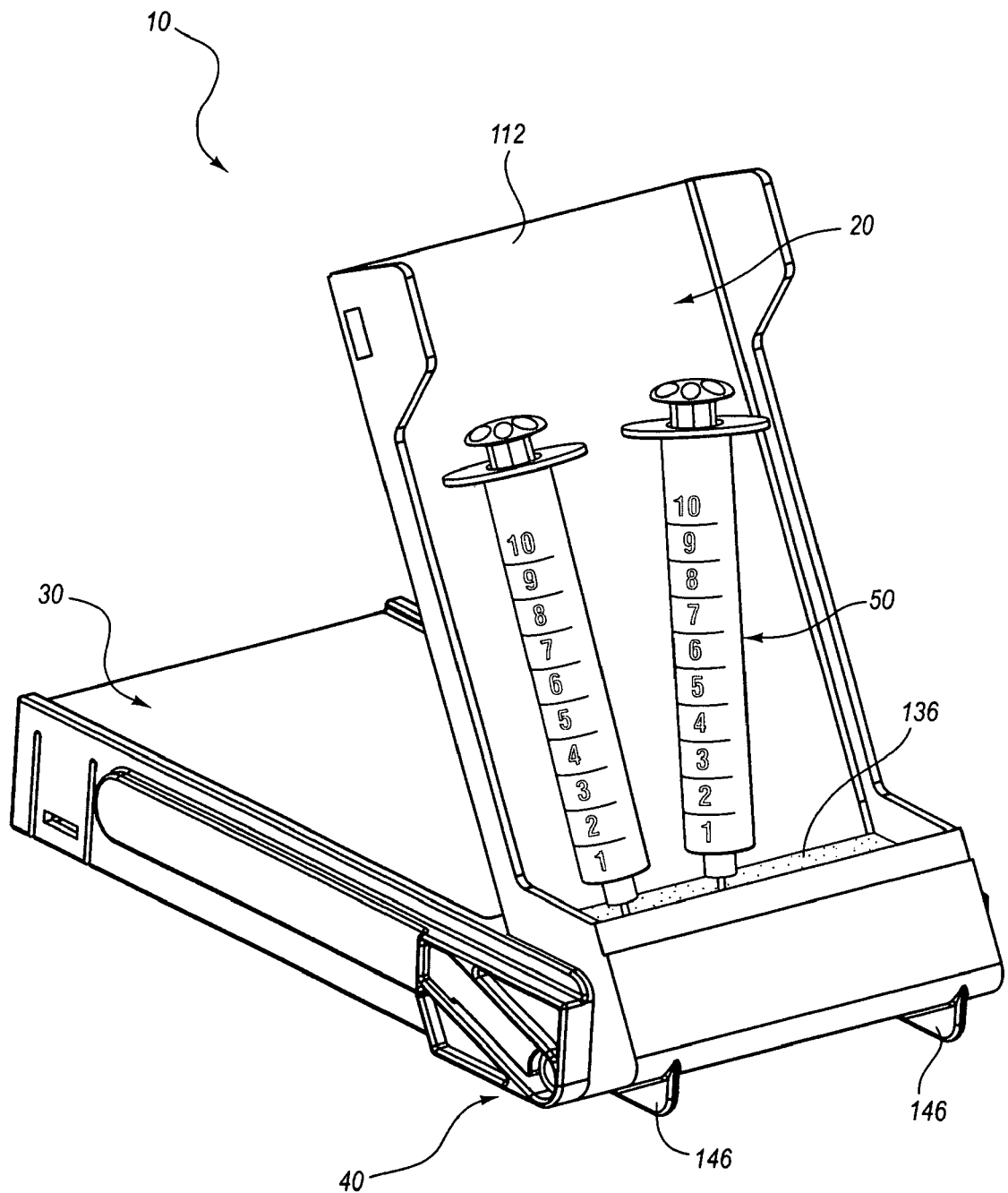
FIG. 1 is a perspective view of illustrative sharps handling device in a stand configuration according to one an aspect of the present invention.

FIG. 1 depicts a perspective view of an embodiment of a sharps handling device 10 that is oriented in a stand configuration. In the illustrated embodiment, the sharps handling device 10 comprises a holder 20 coupled to a base 30 at a hinge 40. The holder 20 can receive one or more sharps devices 50 therein and is configured to hold the one or more sharps devices 50 in a conveniently accessible position during the course of a medical procedure. For example, in some embodiments, a medical practitioner can insert a sharps device 50 (e.g., a partially emptied syringe) in the holder 20 in a generally upright position for temporary storage during a medical procedure, and can remove the sharps device 50 for additional use (e.g., to completely empty the syringe) at a later stage of the medical procedure. The holder 20 can include a support wall 112 that acts as backstop for deflecting sharps devices 50 toward an insertion cushion 136. The support wall 112 thus can provide a practitioner with a relatively large target at which to direct the sharps devices 50 for insertion. Various embodiments of the sharps handling device 10 can be used with one or more varieties of sharps devices 50, such as, for example, needle-bearing syringes, trocars, and/or scalpels.

Figure 9:
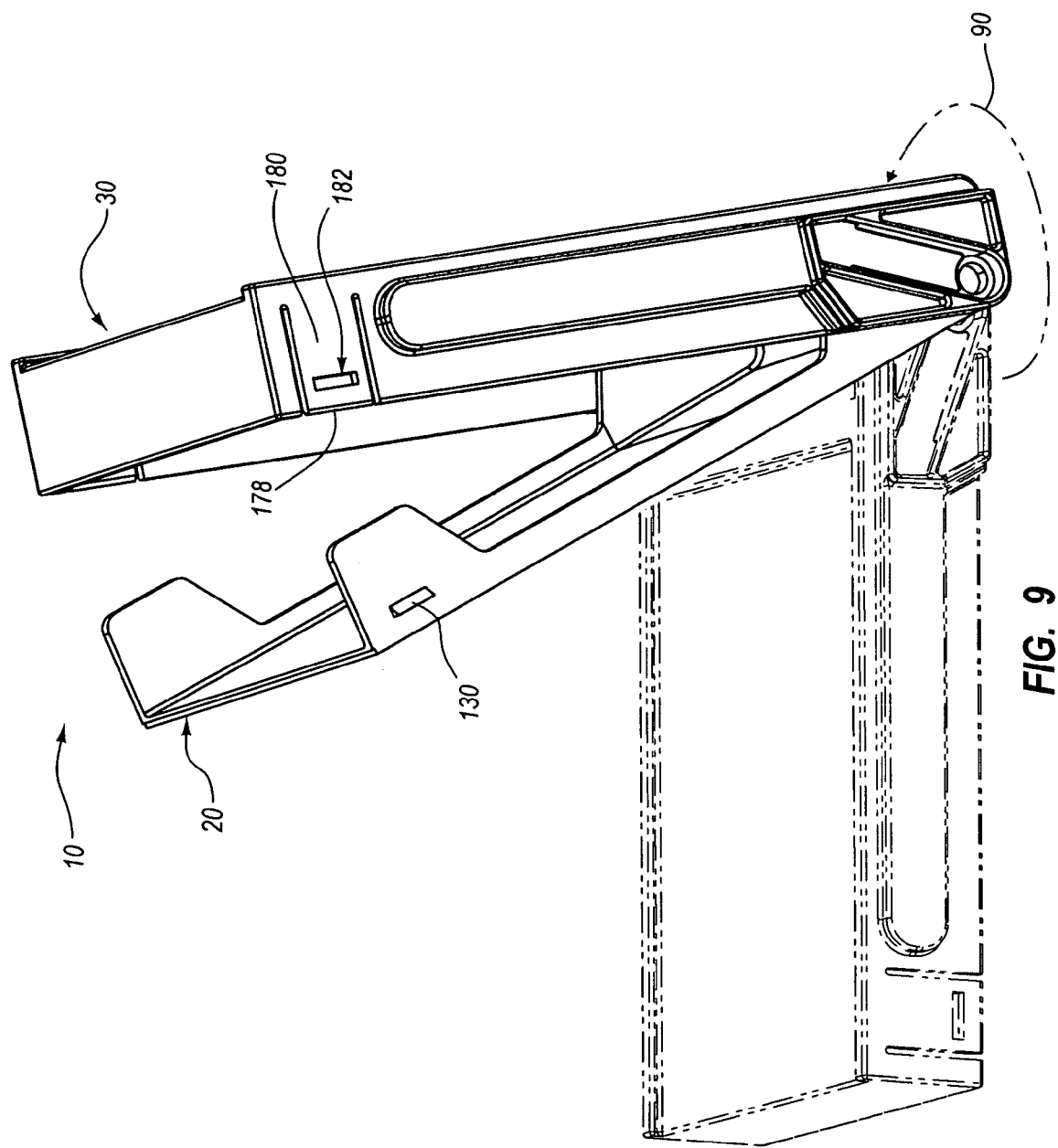
FIG. 9 is a perspective view of the sharps handling device of FIG. 1 being transitioned to a container configuration.
Figure 10:
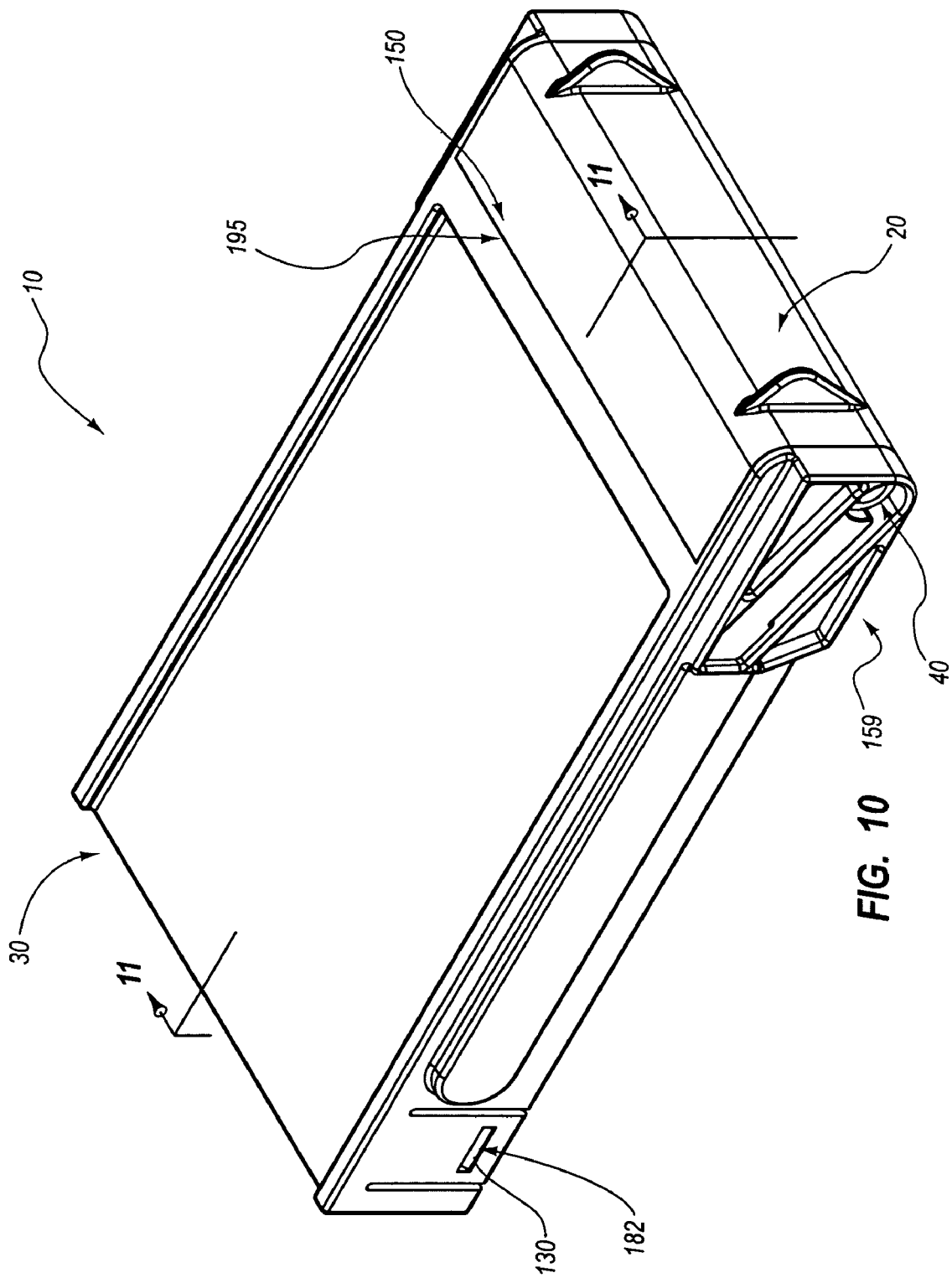
FIG. 10 is a perspective view of the sharps handling device of FIG. 1 in a container configuration according to one aspect of the present invention.

Once the sharps handling device 10 is no longer desired for temporarily storing the one or more sharps devices 50 in an accessible manner, such as may occur once a medical procedure is complete, the holder 20 and the base 30 can be rotated relative to one another about the hinge 40 to securely close the sharps handling device 10 in a closed container configuration (see FIGS. 9 and 10). In various embodiments, sharps devices 50 that have been placed within the holder 20 can thus be substantially fully encased by the closed sharps handling device 10 in a safe and convenient manner without removing the sharps device 50 from the holder 20. In many embodiments, it can be difficult to reopen the sharps handling device 10 once it has been closed such that the sharps handling device 10 can advantageously be used as a sharps disposal container.

In further embodiments, the sharps handling device 10 can be arranged in a shipping configuration (see FIG. 5) in which the holder 20 is nested within the base 30. The stowed configuration can advantageously define a low profile that is well-suited for the storing or transporting of multiple sharps handling devices 10. The sharps handling device 10 can be readily and conveniently transitioned from the shipping configuration to the stand configuration for use.

Figure 2:
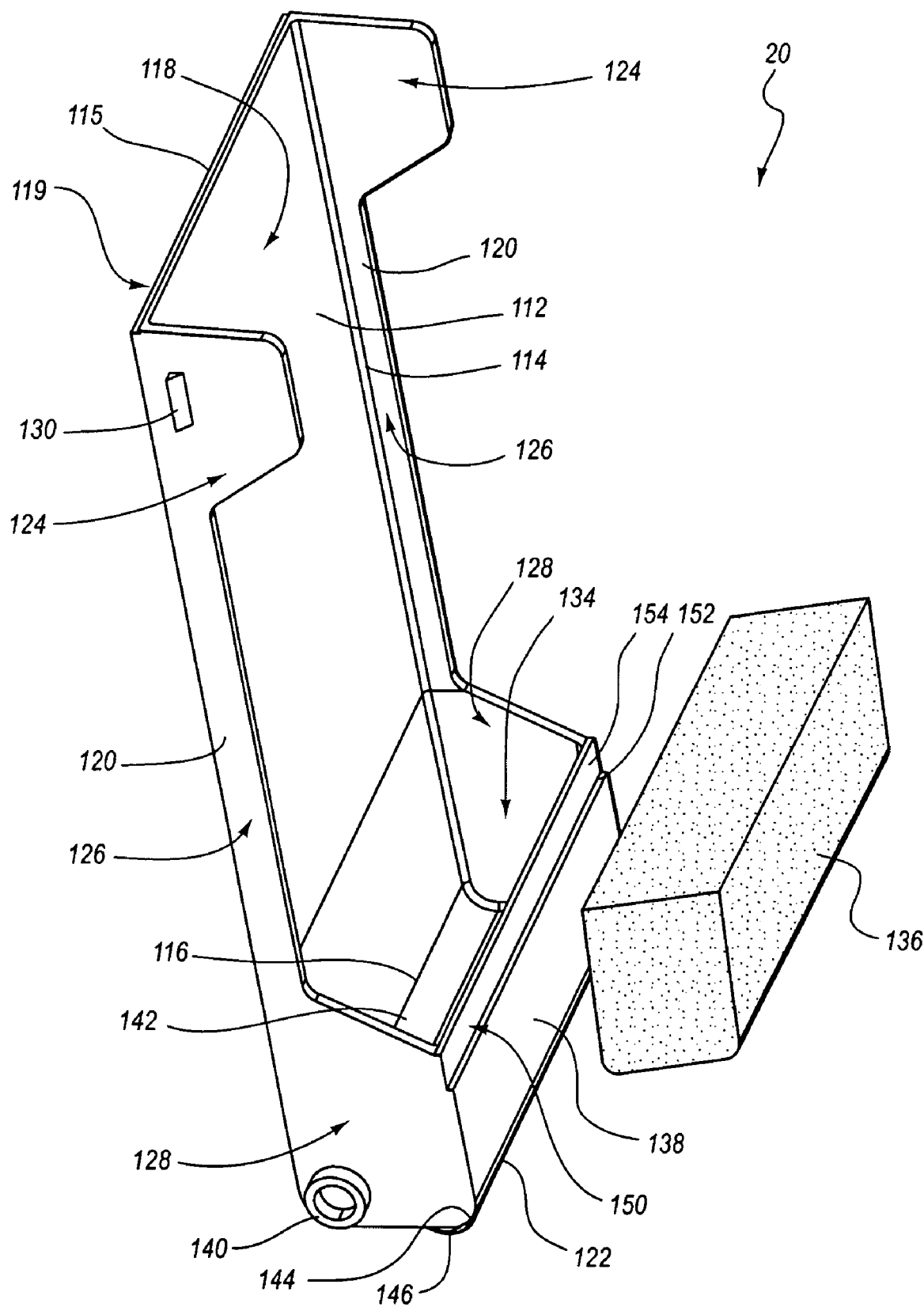
FIG. 2 is an exploded perspective view of an illustrative holder of the sharps handling device of FIG. 1 according to one aspect of the present invention.

With reference to FIG. 2, in certain embodiments, the holder 20 comprises a support wall 112. The support wall 112 can be substantially elongate and can define a relatively large surface area. For example, in the illustrated embodiment, the support wall 112 is substantially rectangular and has side edges 114 that are longer than a top edge 115 and a bottom edge 116, respectively. The support wall 112 can define a forward-facing sharps contact surface 118 that extends between the side edges 114 and between the top and bottom edges 115, 116 of the support wall 112. The support wall 112 can also comprise a rear surface 119 opposite the sharps contact surface 118. In some embodiments, the rear surface 119 can be substantially planar or flat, although other configurations are possible. Directional terms such as side, top, bottom, forward, rear, etc., are used herein by way of convenience and not limitation in referring to the figures. While these terms can correspond with the orientations of various embodiments depicted in the figures, it is noted that other suitable arrangements and orientations are possible.

With continued reference to FIG. 2, in some embodiments, the holder 20 includes one or more sidewalls 120 that extend from the side edges 114 of the support wall 112. The holder 20 can further include a bottom wall 122 that extends from the bottom edge 116 of the support wall 112. In some embodiments, one or more of the sidewalls 120 vary in height along a length thereof. For example, in the illustrated embodiment, each sidewall 120 defines a tab region 124 at its top end that is relatively tall, a side rail region 126 at a more central position that is relatively short, and a cavity region 128 at its lower end that is also relatively tall.

In certain embodiments, the tab region 124 can define a lock protrusion 130. The lock protrusion 130 can be angled such that it slopes outwardly toward a back end thereof. As further discussed, below, the lock protrusion 130 can be configured to cooperate with a portion of the base 30 to secure the sharps handling device 10 in a closed configuration.

In some embodiments, the side rail regions 126 of the sidewalls 120 can provide for relatively unobstructed access to the holder 20. For example, as a practitioner inserts a sharps device 50 into the holder 20 to a position such as, for example, either of the positions of the sharps devices 50 shown in FIG. 1, the relatively low profile of the side rail regions 126 can permit the fingers and/or thumb of the practitioner that grasp the sharps device 50 to approach or touch the support wall 112 substantially without hindrance from the sidewalls 120. Accordingly, in some embodiments, the illustrated holder 20 provides a greater space in which a practitioner can maneuver a sharps device 50 than do certain embodiments in which the height of the sidewalls 120 is not reduced in the side rail regions 126.

The cavity regions 128 of the sidewalls 120 can cooperate with other portions of the holder 20 to define a cushion cavity 134 that is configured to receive a cushion 136. For example, in the illustrated embodiment, the cavity regions 128 of the sidewalls 120 cooperate with a bottom portion of the support wall 112, the bottom wall 122, and a front wall 138 of the holder 20 to define the cushion cavity 134.

The cushion 136 can be retained in the cushion cavity 134 in any suitable manner. For example, in some embodiments, the cushion 136 is slightly larger than the cushion cavity 134 and can be maintained within the cushion cavity 134 via a compression fit or friction fit engagement. In some embodiments, the cushion 136 is adhered to holder 20. In other embodiments, rather than being received within a cavity 134, the cushion 136 can be integrally formed with the holder 20.

The cushion 136 can comprise any suitable material, and in many embodiments, is configured to receive a sharp or pointed end of a sharps device 50 without dulling the device. The cushion 136 can comprise a material configured to support the sharps device 50 and to readily release the device 50 when it is removed by a user. In some embodiments, the cushion 136 can comprise a resilient material that is configured to elastically deform such that the material substantially returns to a previous state upon removal of a sharps device 50. For example, the cushion 50 can comprise a spongy or elastomeric material. In another embodiment, cushion 50 comprises a non-coring securement material. In other embodiments, the cushion 136 can comprise a material that substantially plastically deforms upon insertion of a sharps device. For example, the cushion 136 can comprise a polyethylene or polystyrene foam. In still other embodiments, the cushion 136 can comprise a material that is configured to tightly hold or providing sealing relative to a sharps device 50 that is inserted therein such that removal of the sharps device 50 from the cushion 136 can be difficult.

In some embodiments, each of the sidewalls 120 can define a pivot protrusion 140 that extends outwardly from the sidewall 120. For example, the pivot protrusion 140 can be positioned in the cavity region 128 of the sidewall 120 and can extend in a direction away from the cushion cavity 134. In some embodiments, the pivot protrusion 140 is shaped as a hollow, substantially cylindrical rim. Other configurations of the pivot protrusion 140 are also possible.

In some embodiments, the sidewalls 120 can provide structural reinforcement to the support wall 112. For example, a relatively large upper portion of the support wall 112 can be spaced from a box-like and structurally sturdy portion of the holder 20 that defines the cushion cavity 134. As shown in FIG. 1, the upper portion of the support wall 112 can extend away from the base 30 such that it does not contact the base 30 and, as a result, is not directly supported thereby. Accordingly, the upper portion of the support wall 112 can be subject to twisting or bending, such as when sharps devices 50 are inserted into the holder 20. With reference again to FIG. 2, the tab regions 124 and the side rail regions 126 of the sidewalls 120 can border the upper portion of the support wall 112 and can inhibit bending or twisting of the support wall 112. For example, in the illustrated embodiment, the sidewalls 120 can cooperate with the support wall 112 to define a profile that substantially resembles a structurally reinforced U-beam.

In further embodiments, the sidewalls 120 can inhibit or prevent sharps devices 50 from laterally tipping out of the holder 20. For example, in the embodiment depicted in FIG. 1, a top portion of a sharps device 50 is shown contacting a side rail region 126 of the holder 20 and being maintained in the holder 20 thereby. The sidewall 120 can protrude from the sharps contact surface 118 at a substantially perpendicular angle, thereby substantially defining a corner-shaped region for receiving the sharps device 50.

In some embodiments, the top edge 124 of the deflection wall 122 is substantially free of a top wall or other forward projection. Such an arrangement can permit relatively unencumbered access to the deflection wall 122. For example, without a wall or other projection at its top edge 124, the holder 20 can provide relatively little obstruction to sharps devices 50 that are introduced to the holder 20 from above.

With continued reference to FIG. 2, in some embodiments, the bottom wall 122 includes a curved transition region 142 that gently slopes away from the support wall 112. The transition region 142 can inhibit bending or breaking of some sharps devices 50 that are forcefully inserted into the holder 20. For example, in some applications, a sharps device 50 can be slid downwardly along the sharps contact surface 118 toward the bottom wall 122 in order to insert a sharpened or pointed end of the device 50 into the cushion 136. However, if more force than is required to implant the device 50 in the cushion 136 is applied, the pointed end of the device 50 can continue beyond the contact surface 112 to the transition region 142, which can redistribute some or all of the excess force so as to move the holder 20, rather than bend or break the device 50. In some embodiments, a front end of the bottom wall 122 can include a transition region 144 such as the transition region 142.

In some embodiments, the bottom wall 122 can include a bottom surface that can aid in positioning the holder 20 so as to be propped against the base 30. For example, in some embodiments, the bottom wall 122 comprises feet 146 (see also FIG. 1), which are discussed below.

With continued reference to FIG. 2, in some embodiments, the front wall 138 of the holder 20 can define a binding region 150, which can include one or more of a ledge 152 and a recessed lip 154. In the illustrated embodiment, the ledge 152 projects rearwardly from a front face of the front wall 138 and is joined with the recessed lip 154. The binding region 150 is described in further detail below with respect to FIGS. 12A and 12B.

Figure 3:
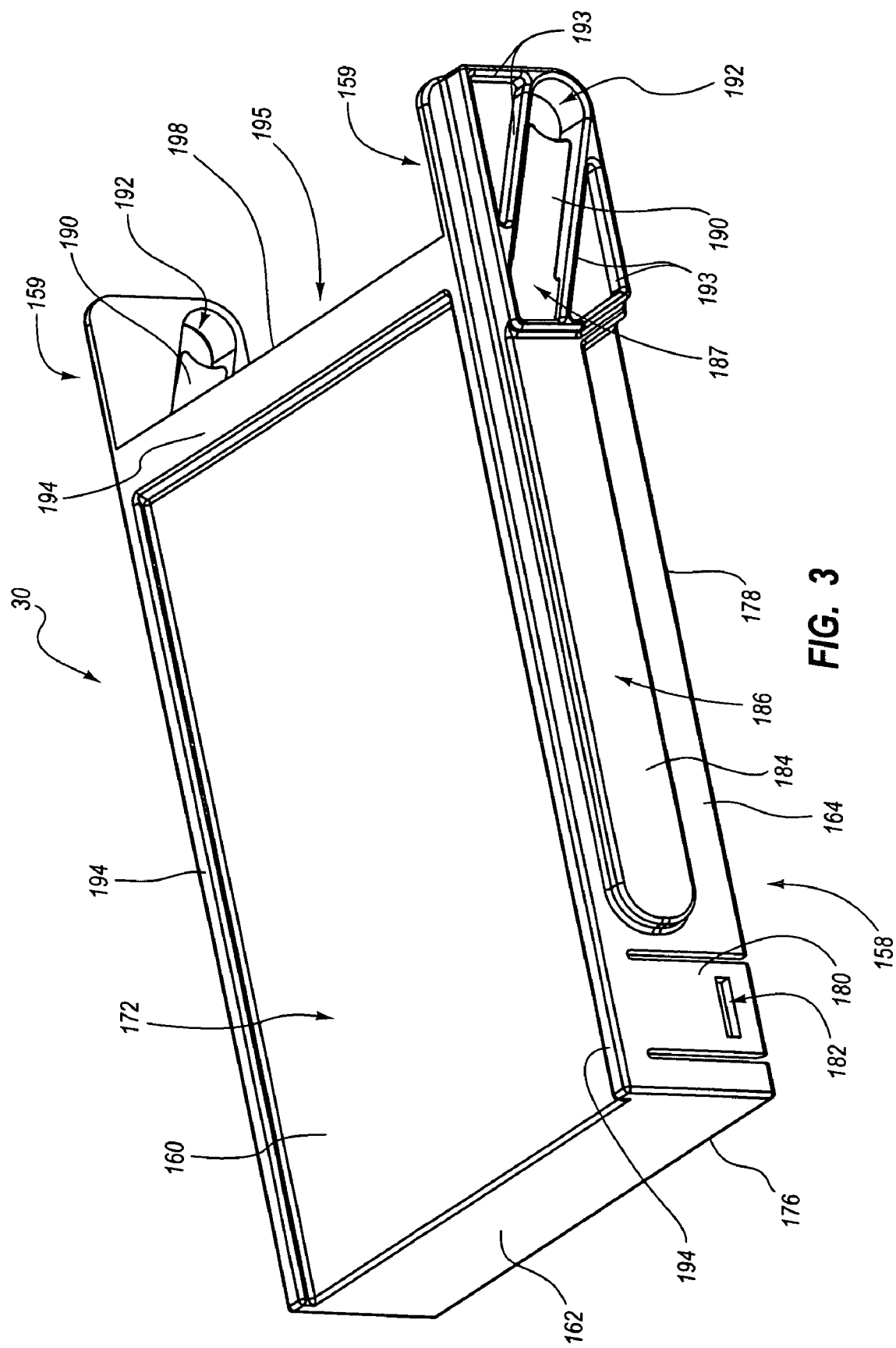
FIG. 3 is a perspective view of an illustrative base of the sharps handling device of FIG. 1 according to one aspect of the present invention.
Figure 4:
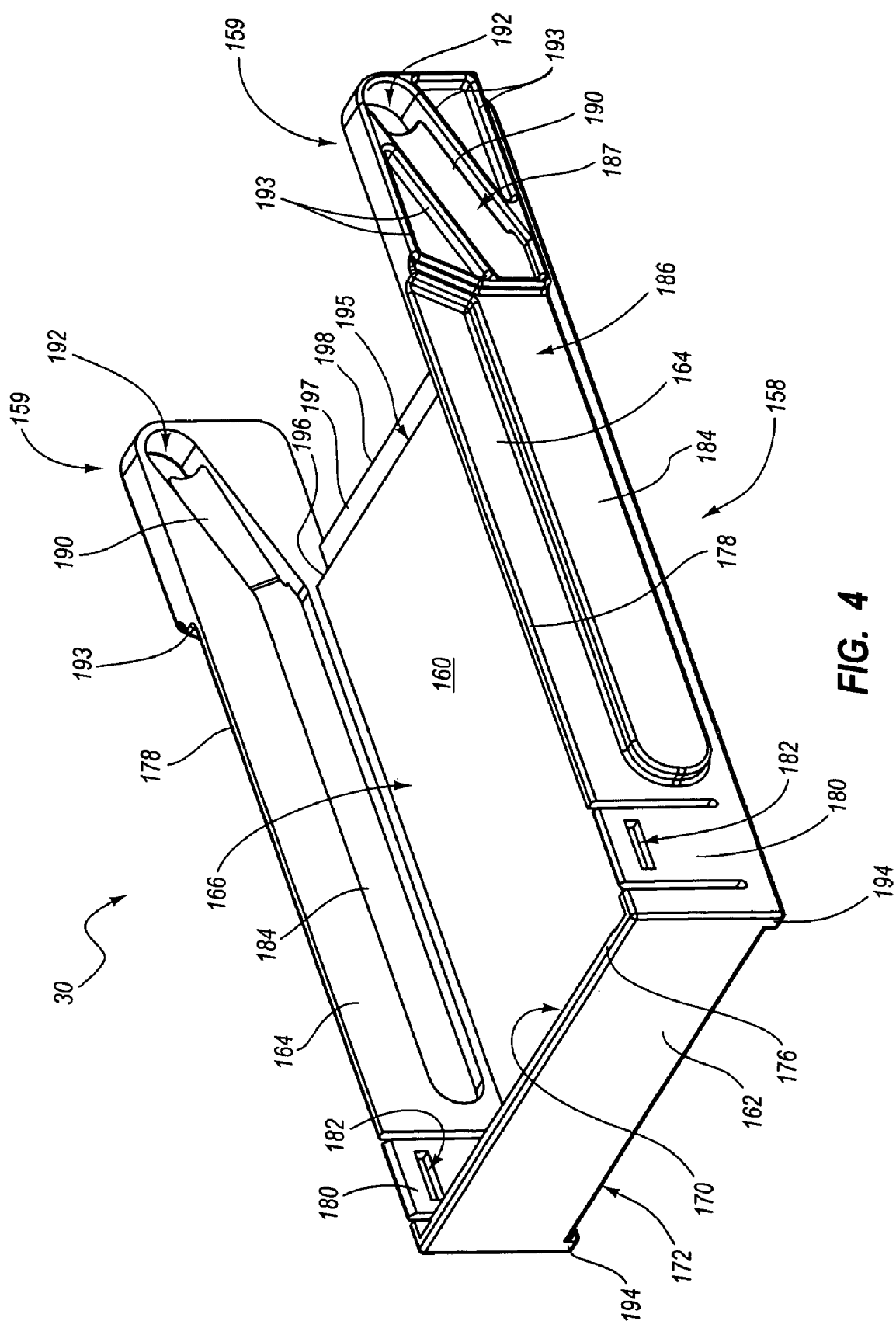
FIG. 4 is another perspective view of the base of FIG. 3 according to one aspect of the present invention.

With reference to FIGS. 3 and 4, in certain embodiments, base 30 defines a generally parallelepiped-shaped portion 158 having two extensions 159 directed from an end thereof. The extensions 159 can also be referred to as hinge locks 159, as further discussed below. The base 30 can comprise a casing wall 160, and can further comprise an end wall 162 and two sidewalls 164, each of which extends substantially perpendicularly from the casing wall 160. In some embodiments, the hinge locks 159 are defined by the sidewalls 164. The casing wall 160 can cooperate with the end wall 162 and the sidewalls 164 to define a containment volume 166. In some embodiments, the containment volume 166 is sufficiently large to receive at least a portion of the holder 20 therein. Other shapes and configurations of the base 30 are also possible.

The casing wall 160 of the base 30 can comprise an interior surface 170 and an exterior surface 172. The interior surface 170 can define at least a portion of the containment volume 166. In some embodiments, the interior surface 170 is substantially planar. For example, in the illustrated embodiment, the interior surface 170 of the casing wall 160 defines a substantially planar rectangle. The rectangular shape of the interior surface 170 of the casing wall 160 can be substantially complementary to the support wall 122 of the holder 20. For example, a width of the interior surface 170 of the casing wall 160, which can correspond to a distance between the sidewalls 164, can be about the same as or slightly larger than a width of the support wall 122 such that at least a portion of the support wall 122 can nest between the sidewalls 164, as further discussed below.

In certain embodiments, a bottom edge 176 of the end wall 162 and a bottom edge 178 of each of the sidewalls 164 can be substantially coplanar. The bottom edges 176, 178 of the base can thus be configured to rest stably on a substantially flat or planar surface. In some embodiments, the bottom edges 176, 178 can comprise a friction-enhancing feature that can aid in inhibiting or preventing movement of the base 30 during use of the sharps handling device 10 in the stand orientation. For example, in some embodiments, the bottom edges 176, 178 can include a roughened surface or a non-slip or adhesive coating.

With continued reference to FIGS. 3 and 4, one or more of the sidewalls 164 can each define a flexible lock tab 180. The lock tab 180 can be configured to elastically deform such that the lock tab 180 resiliently returns to an original position after minor deviations from the position. The lock tab 180 can comprise a lock slit 182 that defines an aperture through the lock tab 180. As further discussed below, in some embodiments, the lock slit 182 can interact with the lock protrusion 130 defined by the holder 20 to securely fasten base 30 to the holder 20 in a closed configuration. In the illustrated embodiment, base 30 comprises a separate lock tab 180 in each of sidewalls 164, and lock tabs 180 are positioned opposite one another at approximately the same distance from the end wall 162.

In certain embodiments, one or more of sidewalls 164 can each define a track 184. Track 184 can be sized and shaped to receive pivot protrusion 140 of holder 20. Track 184 can include a stowage portion 186 that is relatively close to interior surface 170 of casing wall 160, and which can extend substantially parallel to the interior surface 170. The track 184 can further include a deployment portion 187 that angles toward the bottom edge 178 of the sidewall 164. In the illustrated embodiment, each sidewall 164 comprises a separate track 184 that mirrors the track 184 of the other sidewall 164, and the tracks 184 are positioned at approximately the same distance from the end wall 162.

In some embodiments, the stowage portion 186 of the track 184 is recessed relative to an inner surface of the sidewall 164. The stowage portion 186 of the track 184 can also protrude outwardly from an outer surface of the sidewall 164, and can thereby define a structural rib that can strengthen the base 30 and inhibit twisting or bending thereof. In some embodiments, the lock tab 180 is positioned between an end of the stowage portion 186 of the track 184 and the end wall 162 of the base 30.

In some embodiments, the hinge lock 159 comprises the deployment portion 187 of the track 184. The deployment portion 187 of the track 184 can include a resilient flange or arm 190 that is biased inwardly. For example, in the illustrated embodiment, opposing resilient arms 190 are biased inwardly toward one another. The deployment portion 187 of the track 184 can terminate in a socket 192, which can be partially defined by an end of the resilient arm 190. The socket 192 can be sized and shaped to receive the pivot protrusion 140 of the holder 20 (see FIG. 2) and to permit rotation of the pivot protrusion 140 therein. For example, in the illustrated embodiment, the socket 192 defines a substantially cylindrical opening having a slightly larger diameter than the diameter of the cylindrical rim defined by the pivot protrusion 140. The socket 192 can be relatively close to the bottom edges 176, 178 of the base 30, which can aid in stabilizing the sharps handling device 10 when it is in the stand configuration.

In some embodiments, the hinge lock 159 portion of the sidewall 164 can include structural reinforcements, such as substantially triangular ribs 193. Additionally, in some embodiments, the hinge lock 159 can be thicker than other regions of the sidewall 164. Structural reinforcements can strengthen the hinge lock 159 against outward lateral deformations, which can aid in tightly securing the pivot protrusion 140 within the socket 192, and thus in securely maintaining a connection between the base 30 and the holder 20.

With continued reference to FIGS. 3 and 4, in some embodiments, the sidewalls 164 and the exterior surface 172 of the casing wall 160 can define a substantially U-shaped raised rim 194. The rim 194 can structurally reinforce the base 30. In some embodiments, the portion of the rim 194 formed by the casing wall 160 can define a binding region 195. As shown in FIG. 4, the binding region 195 can include a ledge 196 that slopes away from the interior surface 170 of the casing wall 160. The ledge 196 can extend to a recessed face 197, and the recessed face 197 can terminate at a binding edge 198. The binding region 195 is discussed further below with respect to FIGS. 12A and 12B.

With reference to FIGS. 5-7, 9, and 10, in certain embodiments, the sharps handling device 10 can be configured to separately define a shipping or stowed configuration (e.g., FIG. 5), a stand configuration (e.g., FIG. 7), and a container configuration (e.g., FIG. 10). In further embodiments, the holder 20 and the base 30 can be coupled to each other when the sharps handling device 10 is in each of the stowed configuration, the stand configuration, and the container configuration. In still further embodiments, the holder 20 and the base 30 can remain coupled to each other as the sharps handling device 10 is transitioned from the stowed configuration to the stand configuration, and can also remain coupled as the sharps handling device 10 is transitioned from the stand configuration to the container configuration.

Figure 5:
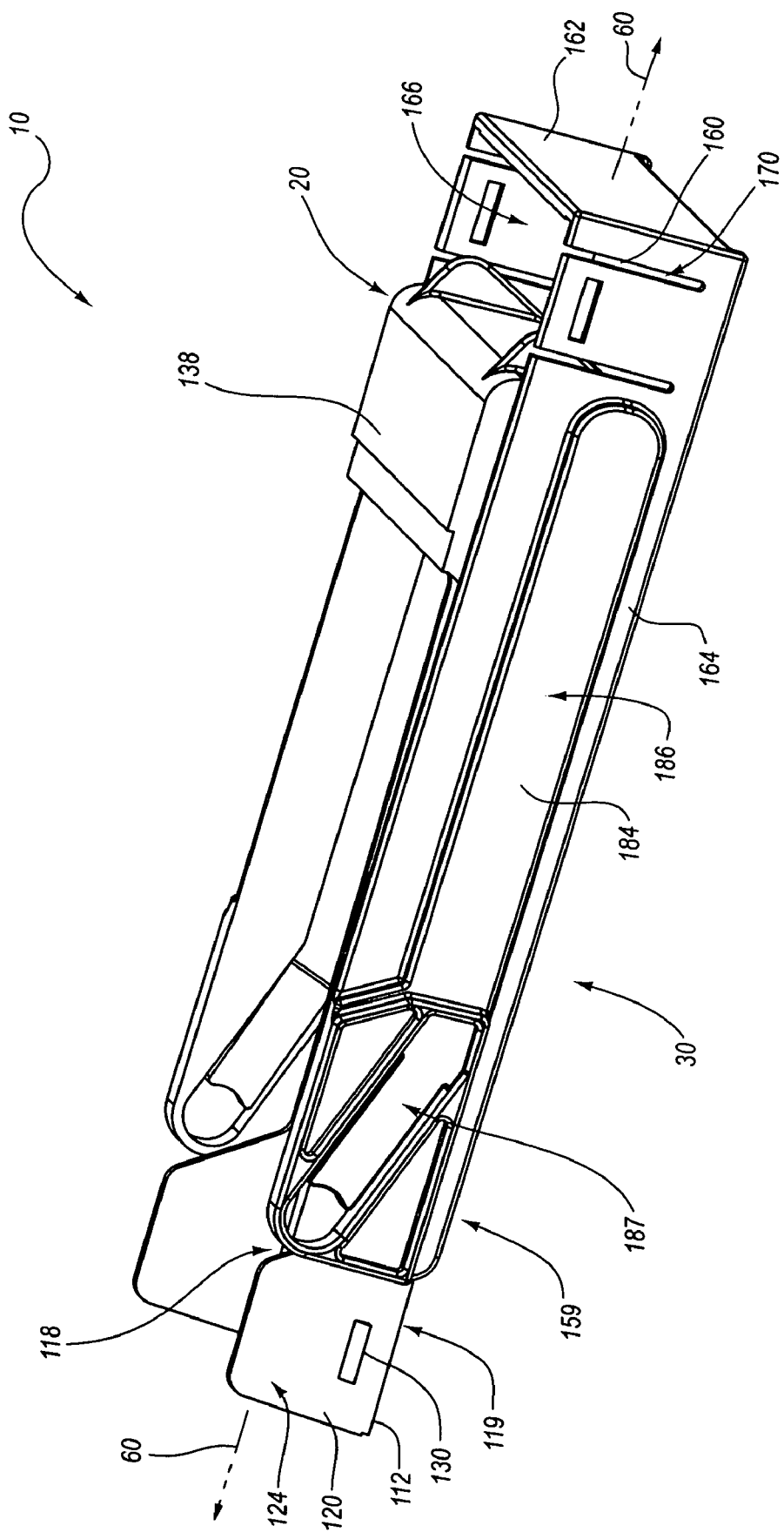
FIG. 5 is a perspective view of the sharps handling device of FIG. 1 in a stowed configuration according to one aspect of the present invention.

FIG. 5 illustrates an embodiment of the sharps handling device 10 in an embodiment of a stowed configuration. In the illustrated embodiment, a portion of the holder 20 is positioned within the containment volume 166 defined by the base 30. Specifically, a majority of the support wall 112 of the holder 20 is within the containment volume 166. The sharps contact surface 118 of the support wall 112 of the holder 20 faces away from the casing wall 160 of the base 30, and the rear surface 119 of the support wall 112 faces the interior surface 170 of the casing wall 160. A small portion of the holder 20, including the front wall 138, protrudes from the containment volume 166, and portions of the tab regions 124 of the sidewalls 120 extend beyond the hinge locks 159 of the base 30. In particular, the lock protrusions 130 of the tab regions 124 are outside of the base 30. In some embodiments, the portions of the holder 20 that are within the base 30 fit snugly therein. Accordingly, in some embodiments, the lock protrusions 130 can extend outwardly further than an interior width defined between the sidewalls 164 of the base 30. The pivot protrusions 140 of the holder 20 (see FIG. 2) can be positioned within the stowage portions 186 of the tracks 184.

With continued reference to FIG. 5, the stowed configuration of the sharps handling device 10 can provide a low profile shape that is convenient for storing multiple sharps handling devices 10 in close proximity to each other, such as for storage or shipping. In further embodiments, the sharps handling device 10 can be stackable when in the stowed configuration, which can also be advantageous for storage or shipping.

As illustrated by the arrows 60 in FIG. 5, in some embodiments, the sharps handling device 10 is moved out of the stowed configuration by urging the holder 20 and the base 30 in substantially opposite directions. The holder 20 and the base 30 can thus translate relative to one another. In particular, the pivot protrusions 140 can slide or otherwise translate within the stowage portions 186 of the tracks 184 toward the deployment portions 187 of the tracks 184.

Figure 6:
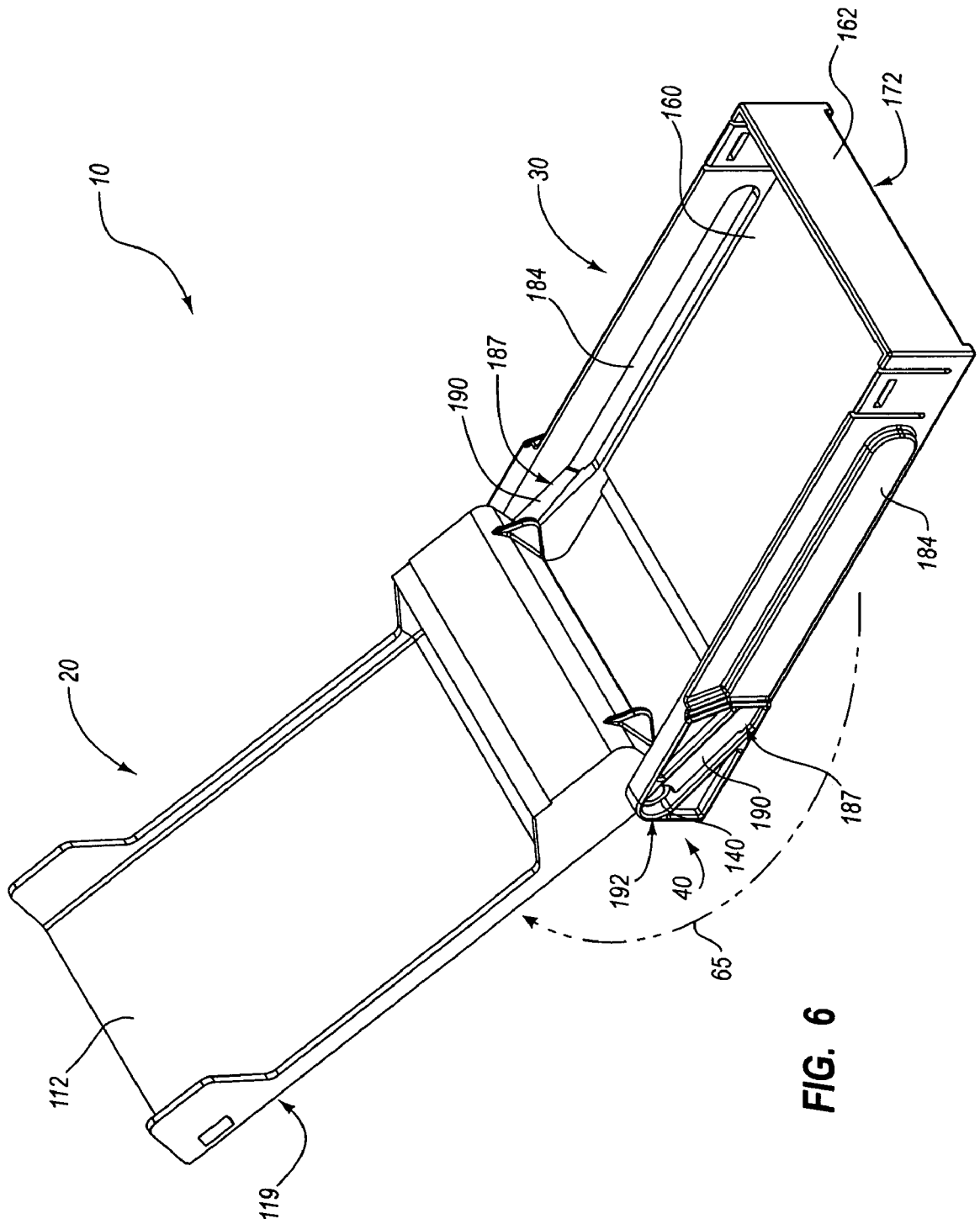
FIG. 6 is a perspective view of the sharps handling device of FIG. 1 in a deployed configuration according to one aspect of the present invention.

FIG. 6 illustrates an embodiment of the sharps handling device 10 in an embodiment of a deployed configuration. In the illustrated embodiment, the pivot protrusions 140 of the holder 20 are within the sockets 192 defined by the base 30, and thereby define the hinges 40 discussed above with respect to FIG. 1. The pivot protrusions 140 are free to rotate within the sockets 192 such that the housing 20 and the base 30 can rotate relative to one another.

In certain embodiments, in order to transition the sharps handling device 10 into the deployed configuration depicted in FIG. 6, the pivot protrusions 140 slide or otherwise translate within the deployment portions 187 of the tracks 184 toward the sockets 192. As the pivot protrusions 140 approach the sockets 192, the pivot protrusions 140 urge the resilient arms 190 outwardly. Once the pivot protrusions 140 are within the sockets 192, the arms 190 are permitted to elastically return toward their original orientation. In some embodiments, the arms 190 resume their original orientation, while in other embodiments, the arms 190 may only partially return to their original orientation. In either case, the arms 190 can substantially lock the pivot protrusions 140 within the sockets 192, thereby substantially preventing translational movement of the holder 20 relative to the base 30.

In some embodiments, it can be desirable to transition the sharps handling device 10 from the deployed configuration to the stowed configuration. For example, in some embodiments, original assembly of the device 10 can include inserting the pivot protrusions 140 into the sockets 192 before advancing the holder 20 into a nested position within the base 30. In certain of such embodiments, in order to move the holder 20 into the stowed configuration, the process just described can be reversed. For example, the arms 190 can be urged outwardly by a sufficient amount to provide clearance for the pivot protrusions 140, and the pivot protrusions 140 can be translated within the tracks 184 toward the end wall 162 of the base 30.

As illustrated by the arrow 65 in FIG. 6, in some embodiments, the sharps handling device 10 can be moved from the deployed configuration to the stand configuration by rotating the base 30 relative to the holder 20 such that the exterior surface 172 of the casing wall 160 approaches the rear surface 119 of the support wall 112 of the holder 20.

Figure 7:
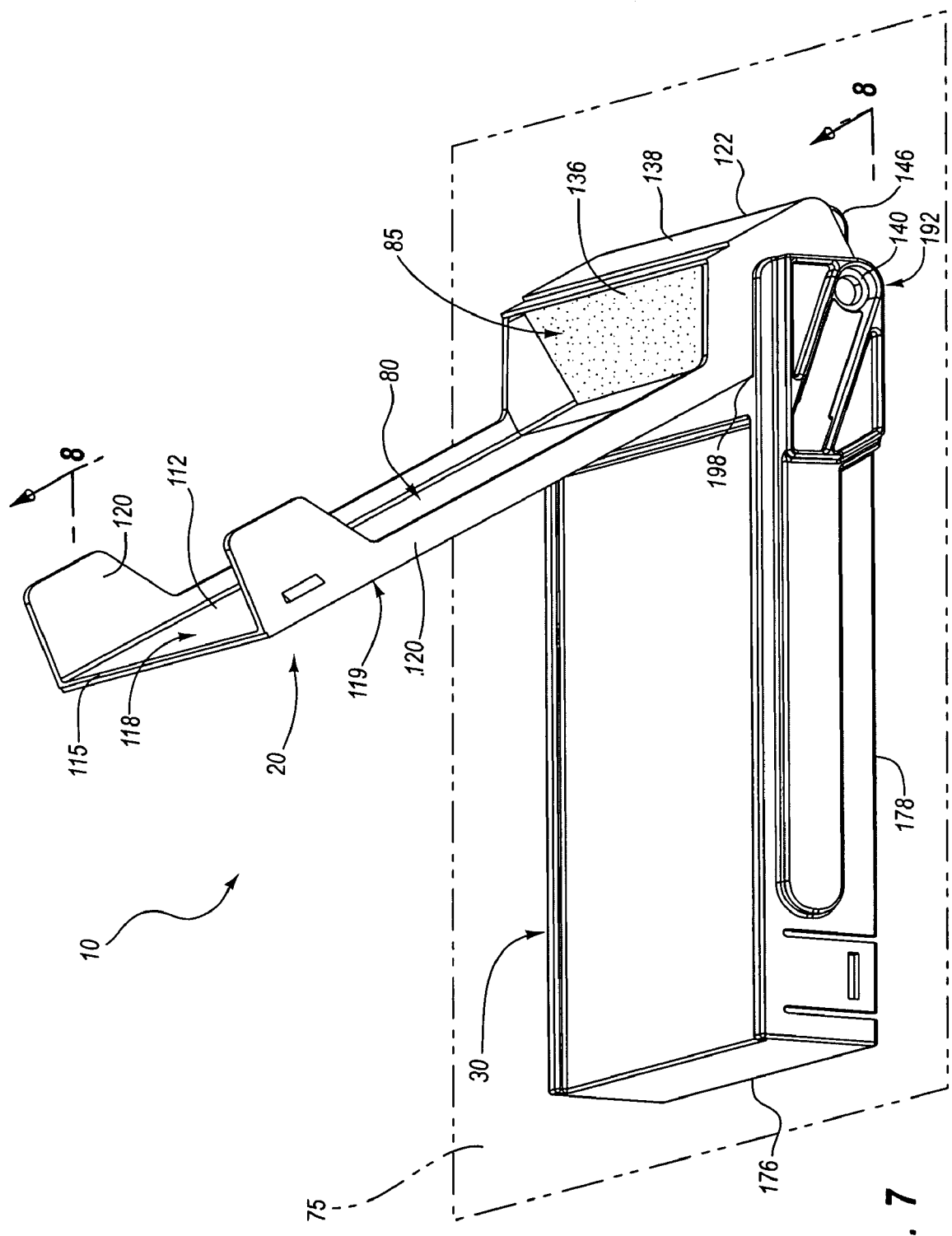
FIG. 7 is another perspective view of the sharps handling device of FIG. 1 shown resting on a substantially planar surface according to one aspect of the present invention.

FIG. 7 illustrates a sharps handling device 10 in a stand configuration according to one aspect of the present invention. In the illustrated embodiment, the rear surface 119 of the support wall 112 of the holder 20 abuts the binding edge 198 of the base 30. The base 30 thus props and maintains the holder 20 in the stand configuration. In particular, contact between the binding edge 198 of the base 30 and the support wall 112 of the holder 20, as well as contact between the socket 192 of the base 30 and the pivot projection 140 of the holder 20, maintain the holder 20 in the stand configuration.

Additionally, feet 146 of the holder 20 can interact with a surface 75 on which sharps handling device 10 is positioned to urge the support wall 112 toward the binding edge 198 of the base 30. In some embodiments, the surface 75 can be substantially planar. Accordingly, in some embodiments, a bottom surface of the feet 146 and the bottom edges 176, 178 of the base 30 can be substantially coplanar.

In some embodiments, when the sharps handling device 10 is in the stand configuration, a surface area of an exposed portion 80 of the sharps contact surface 118 can be substantially larger than a surface area an exposed portion 85 of the cushion 136. For example, in the illustrated embodiment, the exposed portion 80 of the sharps contact surface 118 is adjacent and substantially perpendicular to the exposed portion 80 of the cushion 136. Each of the exposed portions 80, 85 is substantially rectangular and defines substantially the same distance between the sidewalls 120 of the holder 20. However, a longitudinal length of the exposed portion 80 of the sharps contact surface 118 (i.e., the distance between the cushion 136 and the top edge 115 of the support wall 112) is substantially greater than a width of the exposed portion 85 of the cushion 136 (i.e., the distance between the sharps contact surface 118 and the front wall 138). In various embodiments, a surface area of the exposed portion 80 of the sharps contact surface 118 can be greater than a surface area of the exposed portion 85 of the cushion 136 by no less than a factor of about 2, about 3, about 4, about 5, about 6, about 7, about 8, about 9, or about 10. In the illustrated embodiment, a surface area of the exposed portion 80 of the sharps contact surface 118 is about 5 times greater than a surface area of the exposed portion 85 of the cushion 136

Because the sharps contact surface 118 of the sharps handling device 10 can be configured to deflect sharps devices 50 that come into contact with it downwardly toward the cushion 136, a target site to which a user of the sharps handling device 10 can direct a sharps device 50 can comprise the combined surface areas of the exposed portions 80, 85 of the sharps contact surface 118 and the cushion 136. Accordingly, the sharps contact surface 118 can advantageously enlarge the target site for insertion of a sharps device 50 into the cushion 136.

As previously discussed, the sidewalls 120 of the holder 20 can reinforce the support wall 112 during insertion of sharps devices 50. In further embodiments, the support wall 112 can comprise a durable, puncture-resistant material in order to withstand contacts made therewith by sharp or pointed portions of the sharps devices 50. Any suitable material is possible, such as, for example, polycarbonate plastic. In some embodiments, the sharps contact surface 118 can comprise one or more additional puncture-resistant layers or layers to aid in reducing scratching or coring of the support wall 112.

Additionally, it can be advantageous for the bottom wall 122 of the holder 20 to be substantially puncture-resistant so as to withstand contact from sharps devices 50 that are forcefully inserted in the holder 20, or to withstand contact from sharps devices 50 that forcefully abut against the bottom wall 122 in the event that the sharps handling device 10 is dropped. In some embodiments, the holder 20 comprises a unitary piece of material, which can comprise, for example, polycarbonate plastic. In further embodiments, the bottom wall 122 can comprise a thickened region. In some embodiments, the bottom wall 122 can be lined with one or more puncture-resistant materials.

Figure 8A:
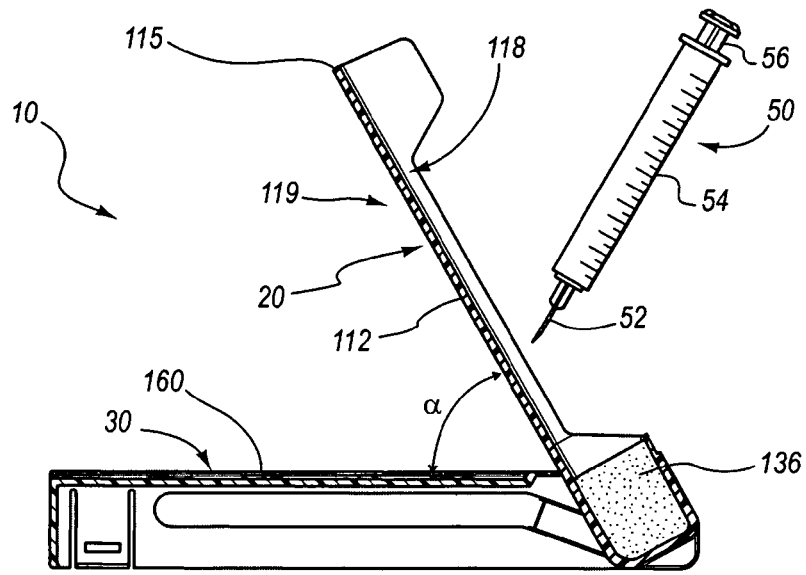
FIG. 8A is a cross-sectional view of the sharps handling device of FIG. 1 taken along the view line 8-8 of FIG. 7 showing a sharps device being directed toward a contact surface of the holder.
Figure 8B:
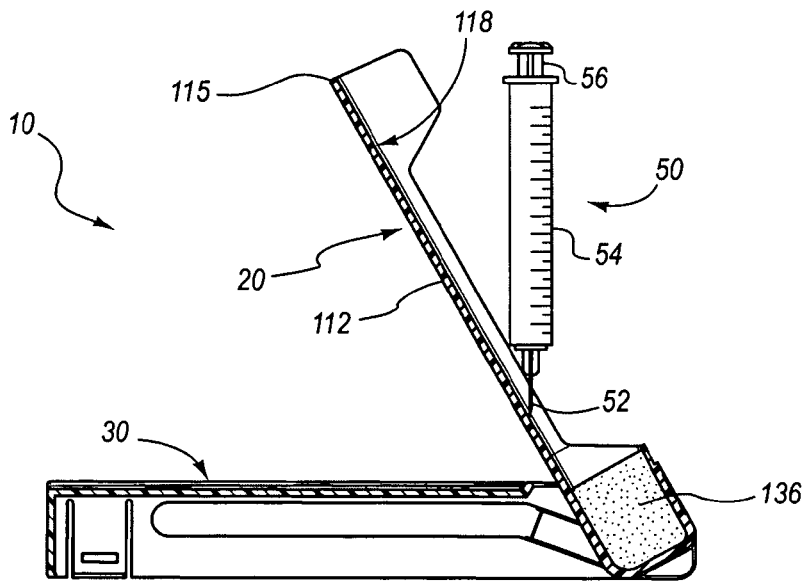
FIG. 8B is a cross-sectional view of the sharps handling device of FIG. 1 taken along the view line 8-8 of FIG. 7 showing the sharps device contacting the contact surface of the holder.
Figure 8C:
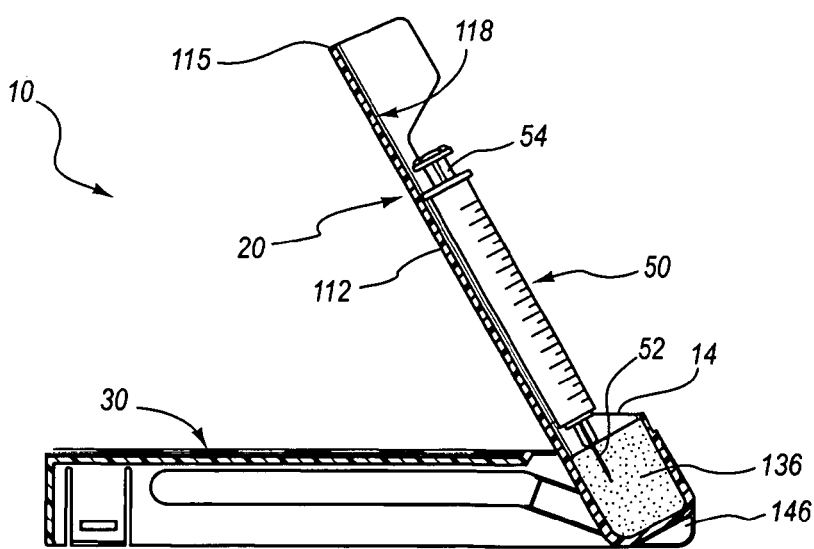
FIG. 8C is a cross-sectional view of the sharps handling device of FIG. 1 taken along the view line 8-8 of FIG. 7 showing the sharps device inserted in a cushion.

FIGS. 8A-8C illustrate the contact surface 118 of the support wall 112 of the holder 20 diverting a sharps device 50 toward the cushion 136 and thereafter supporting the sharps device 50 in a substantially upright orientation. The support wall 112 can be angled relative to the casing wall 160 of the base 30. Additionally, the support wall 112 can extend away from the base 30 in such a manner that the top edge 115 of the support wall 112 is over the base 30. The rear surface 119 can face substantially toward the base 30 and the contact surface 118 can face substantially away from the base 30.

In some embodiments, the deflection characteristics of the support wall 112 can depend on an angle $\alpha$ that the support wall 112 makes with the casing wall 160 of the base 30. Additionally, the amount of support that the support wall 112 can provide to the sharps device 50 can depend on the angle $\alpha$. In some embodiments, the deflection and support characteristics of the support wall 112 for a given application are balanced in determining an angle $\alpha$ for a particular sharps handling device 10. In some embodiments, the angle $\alpha$ can be selectively adjusted for the handling device 10 depending on the applications for which it is to be used. In various embodiments, the angle $\alpha$ is within a range of between about 30 degrees and about 90 degrees, between about 30 degrees and about 75 degrees, between about 30 degrees and about 60 degrees, between about 45 degrees and about 90 degrees, between 45 degrees and about 75 degrees, between 45 degrees and about 60 degrees, between about 50 degrees and about 90 degrees, between about 50 degrees and about 80 degrees, between 50 degrees and about 70 degrees, or between about 50 degrees and about 60 degrees.

As shown in FIG. 8A, in certain embodiments, the sharps device 50 can comprise a syringe that includes a needle 52, a barrel 54, and a plunger 56. In many embodiments, the sharps contact surface 118 can be configured to deflect the needle 52 toward the cushion 136 when the needle is originally directed downwardly toward the contact surface 118 and at a non-perpendicular angle relative to the contact surface 118.

As shown in FIG. 8B, as the illustrated sharps device 50 is deflected toward the cushion 136, the needle 52 slides along the contact surface 118. The sharps device 50 can rotate relative to the contact surface. In the illustrated embodiment, the rotation is counter-clockwise.

As shown in FIG. 8C, as the illustrated sharps device 50 continues to rotate relative to the contact surface 118, the barrel 54 can eventually contact the contact surface 118, which can pivot the sharps device 50 so as to move the needle 52 away from the contact surface 118. In some embodiments, the barrel 54 can be substantially flat against the contact surface 118 as the needle 52 enters the cushion 136. In other orientations, only a portion of the barrel 54 contacts the contact surface 118 when the sharps device 50 is being supported by the support wall 112.

The support wall 112 can support the sharps device 50 in a substantially upright position so as to be readily accessible for additional use. Such a substantially upright position can be substantially vertical or can be angled relative to the vertical. For example, the various positions illustrated in FIGS. 1 and 8C can each be considered substantially upright.

With continued reference to FIG. 8C, in some embodiments, the feet 146 can aid in inhibiting or preventing the holder 20 from tipping forward as the sharps device 50 is inserted in the cushion 136. The feet 146 can additionally inhibit or prevent the holder 20 from tipping forward under the load of the sharps device 50 once it has been inserted in the holder 20.

A height of the plunger 56 within the barrel 54 can depend on the amount of contents of the syringe 50 that have been used in a medical procedure. In various embodiments, the syringe 50 can be used multiple times over the course of a single medical procedure such that the height of the plunger 56 can change between subsequent insertions into the cushion 136. In many embodiments, a longitudinal length of the contact surface 118 is sufficient to support any height of a given plunger 56, which can allow for the entire sharps device 50 to be enclosed within the sharps handling device 10 when it is transitioned to a container configuration. In other embodiments, the plunger 56 or other portions of a sharps device 50 can extend upwardly beyond the top edge 115 of the support wall 112.

FIG. 9 illustrates an embodiment of the sharps handling device 10 being rotated from the stand configuration (see FIG. 7) to a container configuration. In some embodiments, the holder 20 is maintained in a substantially fixed position or is moved only slightly as the transition to the container configuration is made, which can aid in maintaining any sharps devices 50 that have been inserted into the holder 20 within the holder 20. Accordingly, in some embodiments, the base 30 is rotated relative to the holder 20 in transitioning to the container configuration, as indicated by the arrow 90. From a perspective focused on the base 30, in such instances, the movement can be described as the holder 20 being rotated relative to the base 30, or further, can be described as the holder 20 and the base 30 being rotated relative to one another.

As the holder 20 and the base 30 approach one another, the lock protrusion 130 of the holder can come into alignment with the lock slit 182 of the base 30. The lock protrusion 130 can be configured to initially contact the bottom edge 178 of the lock tab 180, and as the holder 20 is further advanced into the base 30, to bend or otherwise displace the lock tab 180 outwardly. Upon further advancement of the holder 20, the lock protrusion 130 can be received within the lock slit 182, and the lock tab 180 can resiliently return toward its original orientation, thereby locking the holder 20 to the base 30.

FIG. 10 illustrates an embodiment of the sharps handling device 10 in the container configuration. The lock protrusion 130 is shown cooperating with the lock slit 182 to lock the holder 20 to the base 30 and thereby maintain the sharps handling device 10 in the container configuration. As previously discussed, the hinge locks 159 can also lock the holder 20 to the base 30, which can also maintain the sharps handling device 10 in the container configuration. Additionally, the binding portion 150 of the holder 20 and the binding portion 195 of the base 30 are shown in contact with each other. As discussed further below, the binding portions 150, 195 can provide a further locking feature for maintaining the sharps handling device 10 in the container configuration. In many embodiments, the sharps handling device 10 can be securely locked and highly resistant to reopening once it has been transitioned to the container configuration. The sharps handling device 10 can thus be well-suited for the disposal of sharps. Moreover, the sharps handling device 10 can advantageously be transitioned to the disposal configuration substantially without moving any sharps that are held by the holder 20 when the sharps handling device 10 is in the stand continued configuration.

Figure 11:
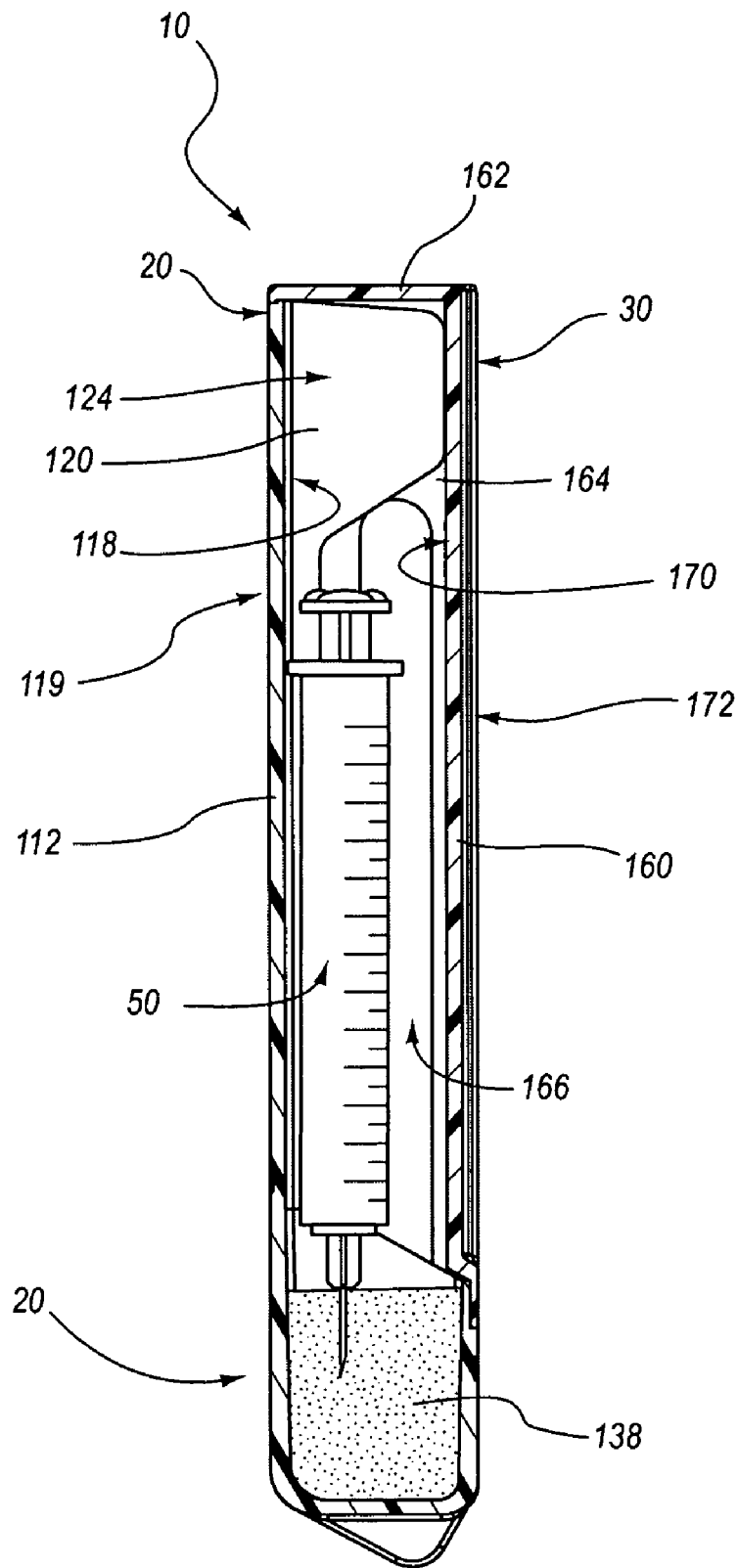
FIG. 11 is a cross-sectional view of the of the sharps handling device of FIG. 1 in the container configuration of FIG. 10 taken along a view line 11-11 of FIG. 10.

FIG. 11 illustrates a cross-sectional view of the sharps handling device 10 in the container configuration. In the illustrated embodiment, a sharps device 50 is fully enclosed within the sharps handling device 10. In particular, the holder 20 and the base 30 cooperate to substantially fully enclose the containment volume 166 defined by the base 30. For example, the support wall 112 of the holder 20 can contact the end wall 162 of the base 30, and the front wall 138 of the holder 20 can contact the casement wall 160 of the base 30 to define both a substantially continuous inner surface and a substantially continuous outer surface of a container arrangement defined by the sharps handling device 10. The rear surface 119 of the support wall 112 and the exterior surface 172 of the casement wall 160 can face outwardly to define an exterior surface of the container arrangement, and the sharps contact surface 118 of the support wall 112 and the interior surface 170 of the casement wall 160 can face inwardly to define an interior surface of the container arrangement. The sidewalls 120, 164 of the holder 20 and the base 30, respectively, can cooperate to enclose the sides of the container arrangement.

In some embodiments, the heightened tab regions 124 of the sidewalls of the holder 20 can contact the interior surface 170 of the base 30 when the sharps handling device 10 is in the closed configuration. The contact can prevent the support wall 112 and the casement wall 160 from crushing the contents of the sharps handling device 10 (e.g., a syringe or other sharps device).

Figure 12A:
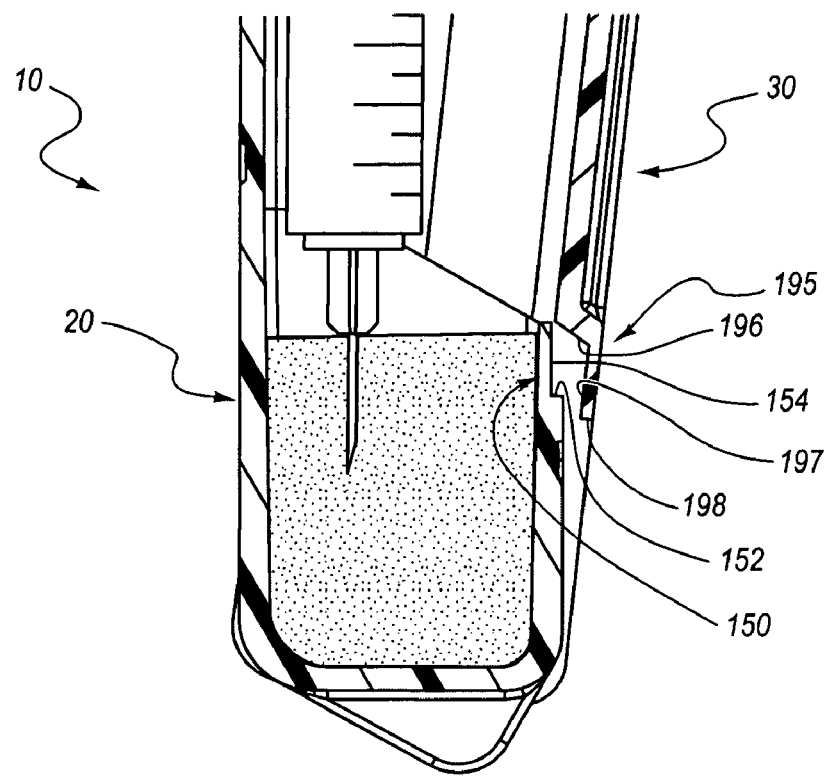
FIG. 12A is a cross-sectional view of a portion of the sharps handling device of FIG. 1 taken along a view line such as the view line 11-11 of FIG. 10 showing binding portions of the sharps handling device being coupled to each other.
Figure 12B:
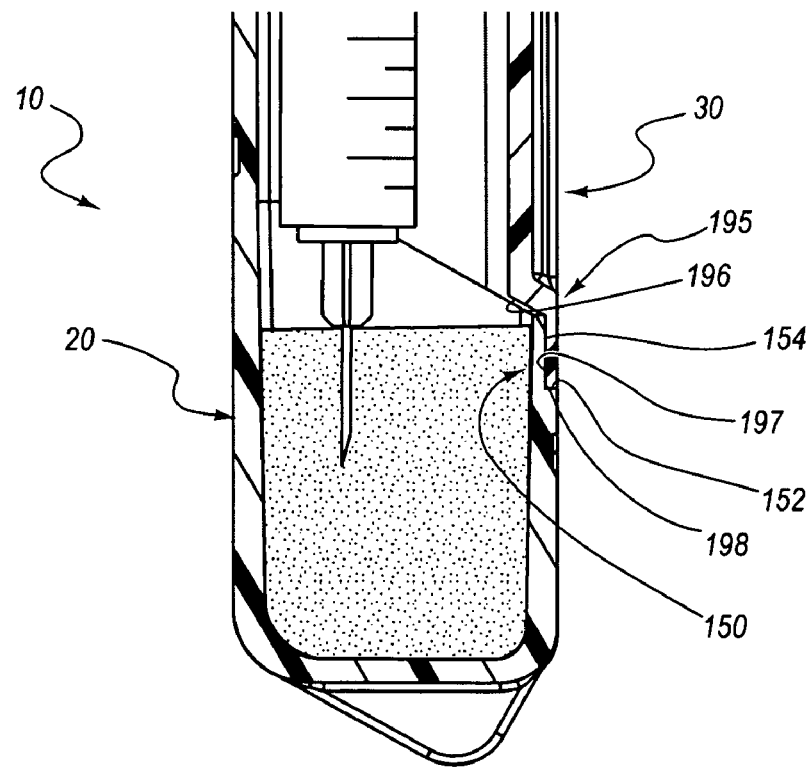
FIG. 12B is a cross-sectional view of a portion of the sharps handling device of FIG. 1 taken along a view line such as the view line 11-11 of FIG. 10 showing the binding portions of the sharps handling device in a coupled engagement.

FIGS. 12A and 12B illustrate the interaction of an embodiment of the binding portions 150, 195 of the holder 20 and the base 30, respectively, as the sharps handling device 10 is transitioned to the container configuration. FIG. 12A depicts the binding portions 150, 195 at a point just prior to initial contact between an edge of the recessed lip 154 and the ledge 196. The ledge 196 is angled such that as the ledge 196 is advanced over the edge of the recessed lip 154, the ledge 196 binds the lip 154 and creates increasing tension therein.

FIG. 12B depicts the sharps handling device 10 in the closed container configuration. As illustrated, the ledge 196 remains in binding contact with the lip 154. Additionally, the binding edge 198 of the base 30 is snapped into tight abutting contact with the ledge 152 of the holder 20. Accordingly, if an upper portion of the base 30 is urged away from the holder 20, the binding edge 198 is forced inwardly toward the intersection of the ledge 152 and the lip 154 of the holder 20 and thus more securely engages the binding region 150 of the holder 20.

With reference again to FIG. 10, as the upper portion of the base 30 is moved away from the holder 20, the engagement between the binding portions 150, 195 can force the base 30 to pivot about the binding portions 150, 195, rather than about the hinge 40. However, the hinge locks 159 can be engaged with the holder 20 when the sharps handling device 10 is in the container configuration such that the hinge lock portions 159 of the base 30 remain substantially fixed as the upper portion of the base 30 is moved away from the holder 20. Because the base 30 can be substantially solid and/or structurally reinforced, as previously discussed, the hinge lock portions 159 of the base 30 can resist rotation of the base 30 about a pivot defined by the binding portions 150, 195. Accordingly, it can be extremely difficult to open the sharps handling device 10 from the closed configuration by, for example, releasing the locks defined by the lock protrusions 130 and the lock slits 182 and thereafter attempting to rotate the holder 20 and the base 30 such that the lock protrusions 130 move away from the lock slits 182.

Figure 13:
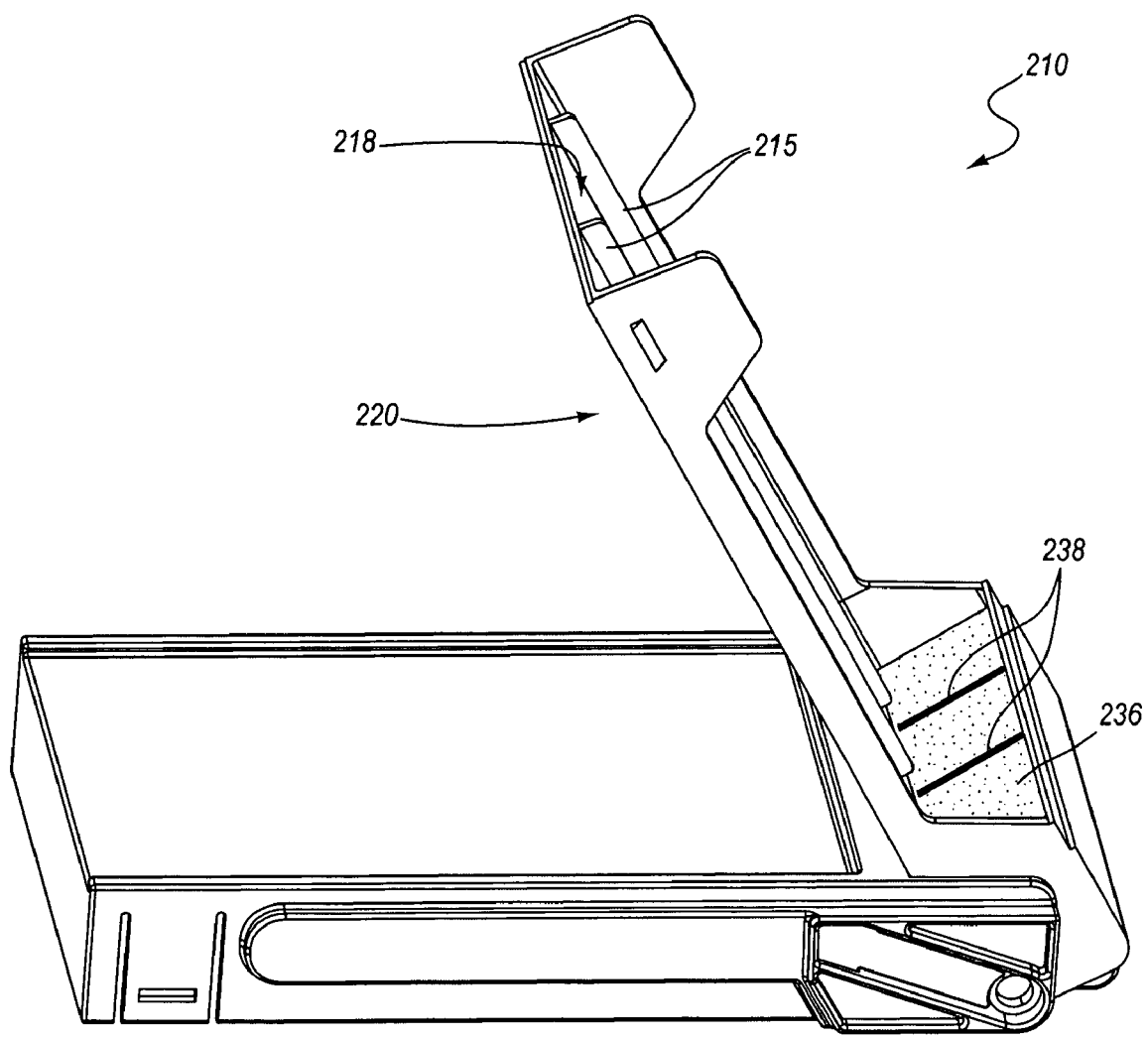
FIG. 13 is a perspective view of another embodiment of a sharps handling device in a stand configuration according to one aspect of the present invention.

FIG. 13 is a perspective view of an embodiment of a sharps handling device 210 such as the sharps handling device 10. The sharps handling device 210 includes a holder 220 that defines support rails 215. The support rails 215 extend away from a sharps contact surface 218 of the holder 220. The support rails 215 can inhibit lateral movement of sharps devices 50 that are inserted into a holder 220.

The sharps handling device 210 further includes a cushion 236 having markings 238 thereon. The cushion markings 238 can provide a guide for placement of one or more sharps devices 50. For example, different regions of the cushion 236 can be composed of separate materials that have differing retention properties such that one material may release sharps inserted therein more readily than another material. The cushion markings 238 can identify regions of the cushion 236 in which the different materials are located. Such an arrangement can identify a portion of the cushion 236 into which reusable sharps can be placed and a portion of the cushion 236 into which single-use sharps can be placed.

In other embodiments, a portion of the cushion 236 can be susceptible to coring and another portion of the cushion 236 can be non-coring. It can be desirable to direct some varieties of sharps devices 50 (e.g., needles) to the non-coring section of the cushion 236, which can be facilitated by the markings 238. In further embodiments, the cushion 236 can be color coded to identify different sections thereof.

Figure 14:
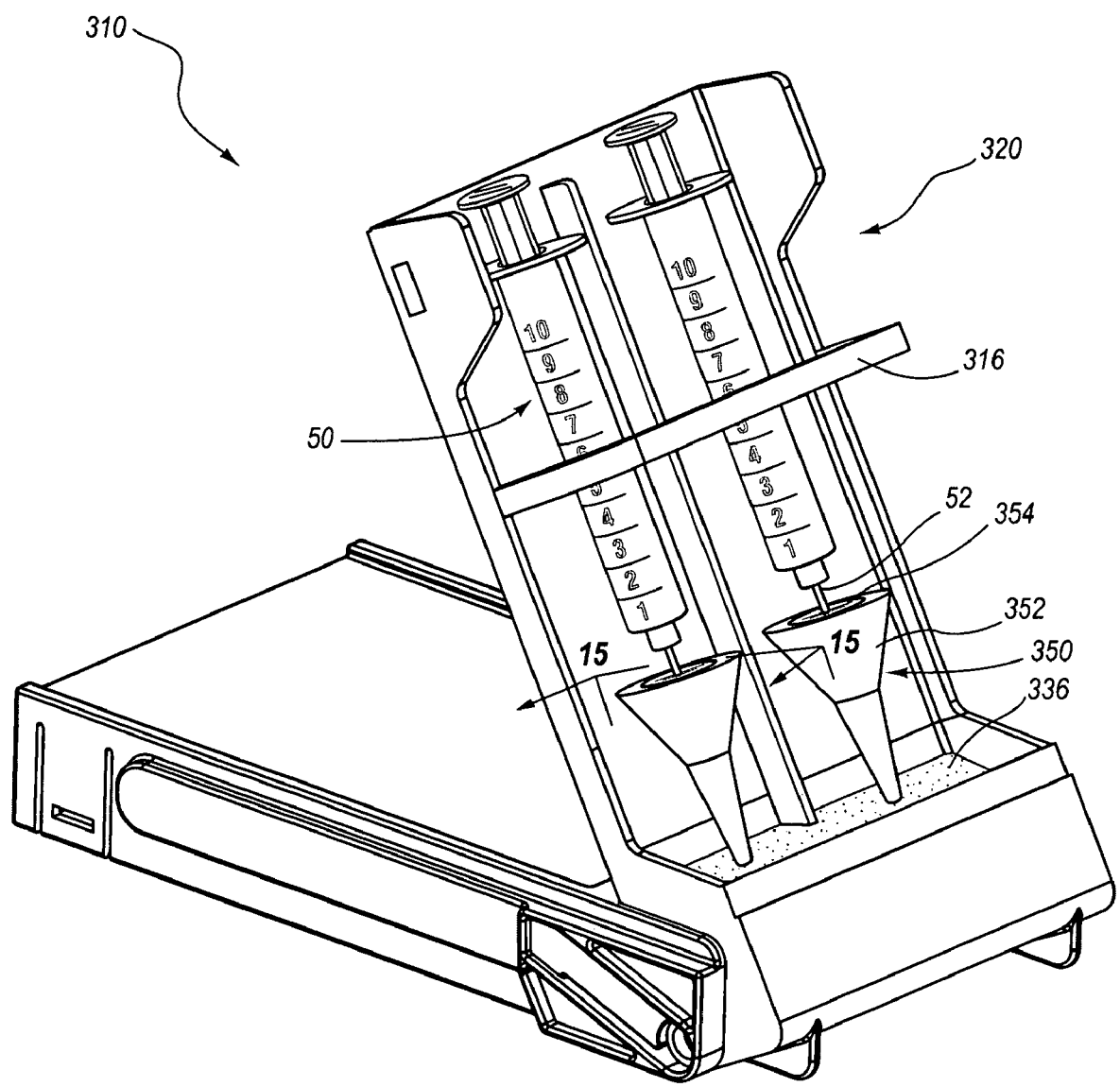
FIG. 14 is a perspective view of another embodiment of a sharps handling device in a stand configuration according to one aspect of the present invention.

FIG. 14 is a perspective view of an embodiment of a sharps handling device 310 such as the sharps handling device 10. The sharps handling device 310 includes a support bar 316 that inhibits or prevents sharps devices 50 from tipping forward out of a holder 320. In some embodiments, the support bar 316 can be well-suited for applications in which it is desirable to maintain sharps devices 50 in a substantially vertical orientation.

In some embodiments the support bar 316 can be configured to aid in the removal of sharps devices 50 that have been inserted into a cushion 336 of a holder 320 (e.g., in an arrangement similar to that shown in FIG. 1). For example, in some embodiments, the support bar 316 can facilitate one-handed removal of a sharps device 50 from the holder 320. The support bar 316 can provide a convenient surface against which a downward force can be applied to the holder 320 as an upward force is applied to the sharps device 50 in order to remove the device 50 from the cushion 336. In some instances, a practitioner can use one or more fingers of a hand to press downwardly on the support bar 316 while using the thumb and one or more fingers of the same hand to grasp and remove the sharps device 50.

In some embodiments, one or more needle guard assemblies 350 can be used with the sharps handling device 310. The guard assemblies 350 can be configured to shield the pointed end of a needle 52 in a substantially permanent fashion to thereby incapacitate the needle 52. The guard assemblies 350 can function in any suitable manner for this purpose.

For example, in some embodiments, a guard assembly 350 can include a housing 352 that is inserted into the cushion 336 or otherwise joined to the holder 320. The housing 352 can include one or more adhesives therein, and can further include at least one membrane 354, which can serve to maintain the one or more adhesives within the housing 352. The one or more adhesives can adhere to the needle 52 once it is inserted into the housing 352 via the membrane 354 such that the needle 52 cannot easily be removed from the guard assembly 350.

Figure 15:
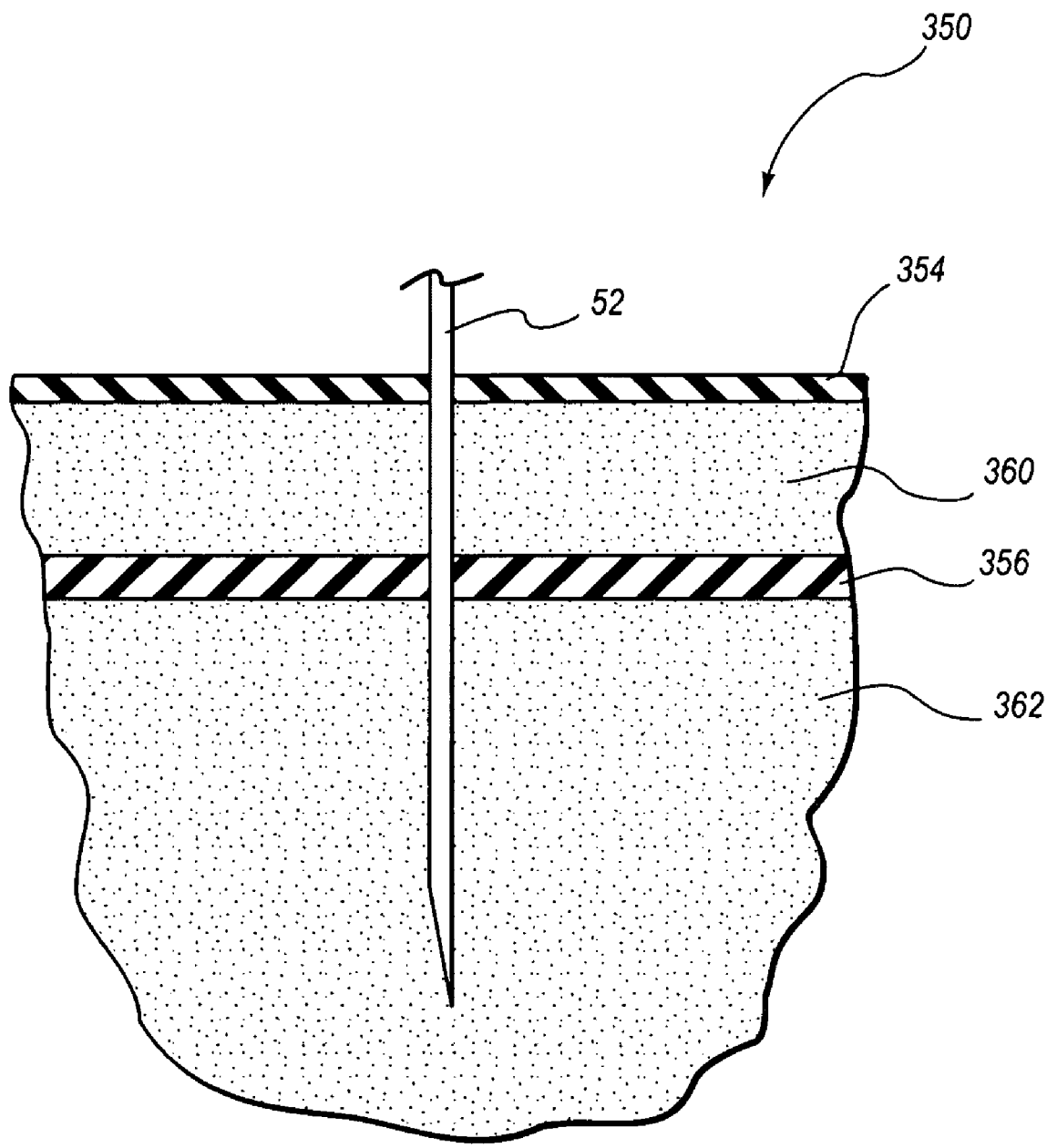
FIG. 15 is a cross-sectional view of a portion of a needle guard taken along the view line 15-15 of FIG. 14 according to one aspect of the present invention.

FIG. 15 depicts a cross-sectional view of a portion of one of the guard assemblies 350 illustrated in FIG. 14 that includes a two-part adhesive. The guard assembly 350 can include a first membrane 354 and a second membrane 356, as well as a first adhesive portion 360 and a second adhesive portion 362. In some embodiments, each of the first and second adhesive portions 360, 362 comprises a separate epoxy. The first adhesive portion 360 can be disposed between the first and second membranes 354, 356, and the second membrane 356 can separate the first adhesive portion 360 from the second adhesive portion 362. When an inserted needle 52 passes through the second membrane 356, the first and second adhesive portions 360, 362 can combine and cure so as to permanently adhere to the needle 52.

Figure 16:
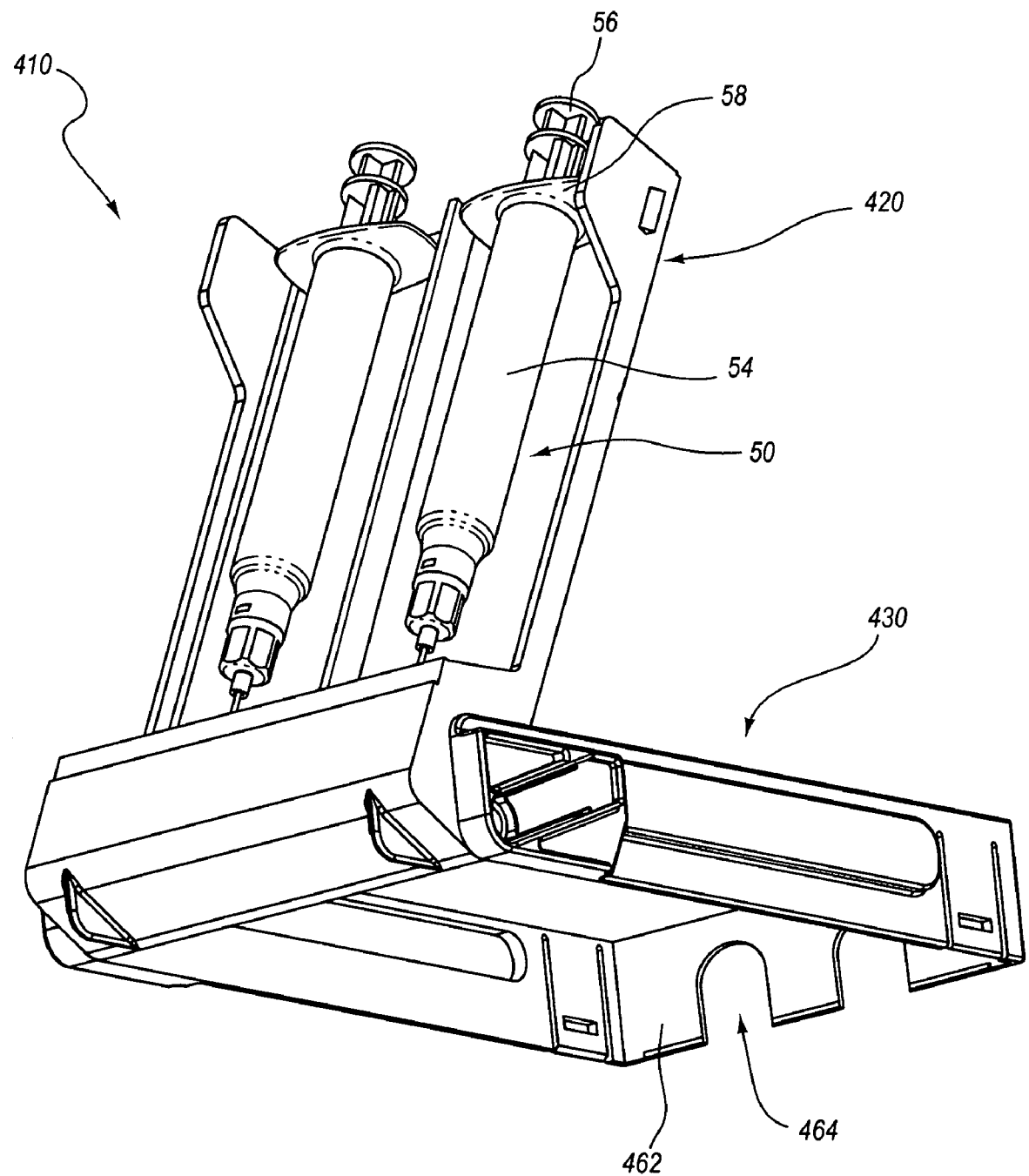
FIG. 16 is a perspective view of another embodiment of a sharps handling device in a stand configuration according to one aspect of the present invention.
Figure 17:
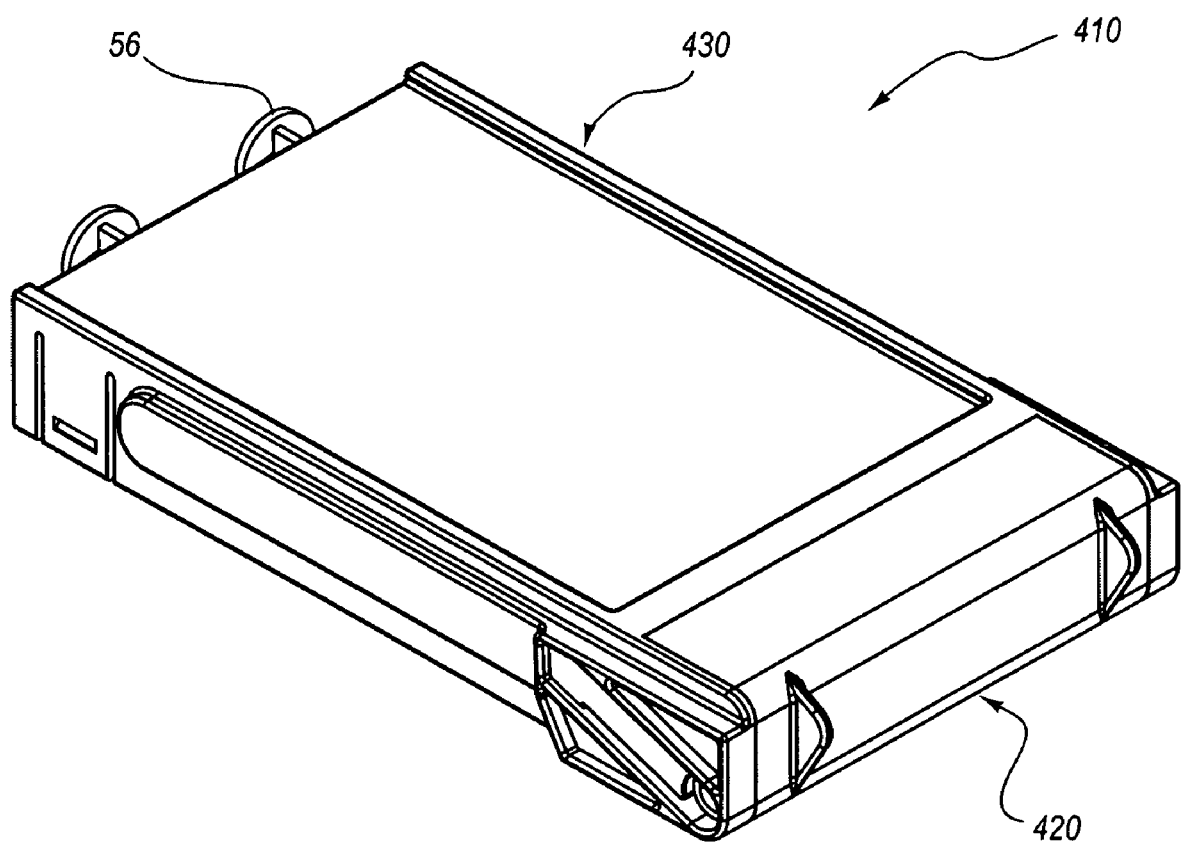
FIG. 17 is a perspective view of the sharps handling device of FIG. 16 in a container configuration according to one aspect of the present invention.

FIGS. 16 and 17 are perspective views of an embodiment of a sharps handling device 410 such as the sharps handling device 10. The sharps handling device 410 can be configured to enclose only a portion of a sharps device 50 that has been inserted into a holder 420. For example, the sharps handling device 410 can include one or more recesses or openings 464 in an end wall 462 of a base 430 through which a portion of a sharps device 50 can extend when the sharps handling device 410 is closed.

As shown in FIG. 16, in some embodiments, a plunger 56 of a syringe 50 can extend beyond an upper edge of the holder 420 when the syringe is inserted in the holder. A portion of a barrel 54 of the syringe, such as a flange 58, can be positioned below the upper edge of the holder 420. As shown in FIG. 17, when the sharps handling device 410 is closed, the plunger 56 can extend through an opening 464 such that it is outside of the sharps handling device 410. The flange 58 can abut an interior surface of the end wall 462 and can aid in maintaining the syringe 50 within the sharps handling device 10.

Some embodiments of the sharps handling device 410 can be of particular utility for applications in which it is desirable to temporarily enclose only a sharpened portion of a sharps device 50, such as, for example, to enclose a needled end of a syringe between medical procedures in which the syringe is to be used. Some embodiments can advantageously reduce manufacturing costs by permitting for a relatively more compact design that contains fewer materials.

Various modifications, changes, and variations apparent to those of skill in the art may be made in the arrangement, operation, and details of the apparatus and methods detailed in this disclosure without departing from the spirit and scope of the disclosure. For example, in some embodiments, the holder 20 can comprise one or more tracks such as the tracks 184 described above and the base 30 comprises one or more pivot protrusions such as the pivot protrusions 140 described above that can interact in a similar manner to transition the sharps handling device 10 among different operational configurations. Thus, it is to be understood that the embodiments described above have been presented by way of example, and not limitation. Any suitable combination of the features described above is contemplated. For example, in various embodiments, support rails 215, the cushion 236, the support bar 316, the guard assemblies 350, and/or the openings 464 can be included in the sharps handling device 10. Moreover, each embodiment recited in the claims that follow is incorporated herein as a separate embodiment.

What is claimed is:

1. A sharps handling device comprising:
   a cushion configured to receive one or more sharp or pointed objects therein;
   a holder defining a cavity, the cushion being positioned within the cavity, the holder comprising a support wall having a sharps contact surface and being positioned at a non-perpendicular angle with respect to a support surface to guide a sharp or other pointed object to the cushion within the cavity of the holder, wherein at least a portion of the sharps contact surface is adjacent to the cavity; and
   a base comprising a casing wall having an interior surface, wherein the interior surface of the casing wall defines at least a portion of a containment volume,
   wherein the holder is pivotally coupled with the base, allowing a user to selectively rotate the base relative to the holder between a stand configuration and a container configuration, and wherein when the base is positioned relative to the holder in a stand configuration, the base supports the holder in a raised orientation such that the support wall of the holder extends upwardly relative to the base and such that the sharps contact surface is configured to deflect one or more sharps or pointed objects downwardly toward the cavity of the holder, and
   wherein when the holder is configured to be coupled with the base in the container configuration, the holder substantially encloses the containment volume defined by the base and in which the holder is locked to the base so as to inhibit the holder from transitioning out of the container configuration once the base is secured in the container configuration relative to the base.

2. The sharps handling device of claim 1, wherein the sharps contact surface of the holder faces away from the casing wall of the base when the holder is in the stand configuration.

3. The sharps handling device of claim 2, wherein the support wall of the holder is configured to define an angle relative to the casing wall of the base when the holder is in the stand configuration such that when a sharps device is inserted in the cushion, the holder can support a portion of the sharps device at a position spaced from the cushion.

4. The sharps handling device of claim 1, wherein the sharps contact surface of the holder is configured to face the interior surface of the casing wall of the base when the sharps handling device is in the container configuration.

5. The sharps handling device of claim 1, wherein a portion of the holder is configured to interact with a surface on which the sharps handling device is rested so as to urge the holder against the base to maintain the holder in the stand configuration.

6. The sharps handling device of claim 5, wherein the portion of the holder comprises one or more surfaces that are substantially coplanar with an edge defined by the base when the sharps handling device is in the stand configuration such that the sharps handling device is configured to rest on a substantially planar surface.

7. The sharps handling device of claim 1, wherein the casing wall of the base contacts and supports the support wall of the holder when the sharps handling device is in the stand configuration.

8. The sharps handling device of claim 1, wherein a portion of the sharps contact surface of the holder and a portion of the cushion are exposed when the holder is in the stand configuration and the cushion is positioned in the holder, and wherein the surface area of the exposed portion of the sharps contact surface is greater than the surface area of the exposed portion of the cushion.

9. The sharps handling device of claim 8, wherein the surface area of the exposed portion of the sharps contact surface is at least twice as large as the surface area of the exposed portion of the cushion.

10. The sharps handling device of claim 1, wherein the base further comprises sidewalls that extend from the casing wall, and wherein the sidewalls cooperate with the casing wall to define the containment volume.

11. The sharps handling device of claim 1, wherein one of the base and the holder comprises a protrusion and the other of the base and the holder comprises a slot configured to receive the protrusion, and wherein the protrusion is received within the slot to thereby lock the holder to the base when the holder is in the container configuration.

12. The sharps handling device of claim 11, wherein the base further comprises a lock tab that includes the slot, wherein the holder comprises the protrusion, and wherein the protrusion is configured to displace the lock tab as the holder is being moved to the container configuration and is configured to engage the slot of the lock tab when the holder is in the container configuration.

13. The sharps handling device of claim 11, wherein the base further comprises a first binding region and the holder further comprises a second binding region, and wherein the first and second binding regions are positioned adjacent one another when the holder is in the container configuration, wherein the first and second binding regions are configured to inhibit movement of the base away from the holder as the protrusion and the slot are separated and urged in opposite directions.

14. The sharps handling device of claim 1, wherein the base further comprises a first binding region and the holder further comprises a second binding region, and wherein the first and second binding regions are positioned adjacent one another when the holder is in the container configuration, wherein the first and second binding regions are configured to inhibit movement of the holder away from the base once the holder has transitioned to the container configuration.

15. A sharps handling device comprising:
   a holder comprising a cushion cavity with a cushion being secured therein and being adapted to secure a sharp or other instrument within the cushion, the cushion cavity being positioned at an end of the holder and being configured to receive one or more sharp or pointed objects therein, the holder further comprising a support wall having a sharps contact surface, wherein at least a portion of the sharps contact surface is adjacent to the cushion cavity; and
   a base coupled to the holder, the base comprising a casing wall having an interior surface that defines at least a portion of a containment volume,
   wherein the holder pivotally coupled with the base such that a user can selectively rotate the base from a stand configuration to a container configuration, wherein the holder is configured to be supported by the base in a raised orientation such that the support wall of the holder extends upwardly from the base when the holder is in the stand configuration, the support wall being positioned at a non-perpendicular angle with respect to a support surface to guide a sharp or other pointed object to the cushion within the cavity of the holder when the sharp inadvertently contacts the support wall as the user attempts to place the sharp within the cushion cavity, and wherein the holder is configured to substantially enclose the containment volume defined by the base such that the sharps contact surface of the holder faces the containment volume when the holder is in the container configuration.

16. The sharps handling device of claim 15, wherein one of the base and the holder comprises a pivot projection and the other of the base and the holder comprises a socket configured to receive the pivot projection, and wherein the pivot projection and the socket are configured to rotate relative to one another as the holder transitions from the stand configuration to the container configuration.

17. The sharps handling device of claim 16, wherein the holder is configured to be coupled with the base in a stowed configuration and is configured to remain coupled with the base as the holder transitions to the stand configuration, and wherein the pivot projection is configured to translate relative to the socket as the holder transitions from the stowed configuration to the stand configuration.

18. The sharps handling device of claim 15, wherein the holder is configured to be coupled with the base in a stowed configuration in which a surface of the support wall that is opposite the sharps contact surface faces the interior surface of the casing wall of the base, and wherein the holder is configured to remain coupled with the base as the holder transitions from the stowed configuration to the stand configuration.

19. The sharps handling device of claim 15, wherein the holder is configured to be coupled with the base in a stowed configuration in which at least a portion of the support wall of the stand is received within the containment volume defined by the base.

20. The sharps handling device of claim 15, wherein the support wall of the holder extends at an angle relative to the casing wall of the base when the holder is in the stand configuration such that the support wall of the holder and the casing wall of the base are non-parallel to one another.

21. The sharps handling device of claim 15, wherein when the holder is in the container configuration, the holder is locked to the base so as to inhibit the holder from transitioning out of the container configuration.

22. The sharps handling device of claim 21, wherein one of the base and the holder comprises a protrusion and the other of the base and the holder comprises a slot configured to receive the protrusion, and wherein the protrusion is received within the slot to thereby lock the holder to the base when the holder is in the container configuration.

23. A sharps handling device comprising:
a holder comprising as support wall and a cushion cavity, the cushion cavity having a cushion secured therein and being adapted to secure a sharp or other instrument within the cushion, the cushion cavity being positioned at an end of the holder, wherein the cushion cavity is configured to receive at least a portion of, and the support wall is configured to contact, one or more sharp or pointed objects to facilitate placement of and securement of the sharp or pointed objects within the cushion; and
a base coupled to the holder, the base comprising a casing wall that defines at least a portion of a containment volume,
wherein the holder separately defines a stowed configuration, a stand configuration and a container configuration, such that when the holder is in a stowed configuration at least a portion of the support wall is nested in the containment volume defined by the base and when the holder is in a stand configuration, the support wall of the holder is substantially outside of the containment volume and extends at a non-perpendicular angle relative to the casing wall of the base, to guide a sharp or other pointed object to the cushion within the cavity of the holder when the sharp inadvertently contacts the support wall as the user attempts to place the sharp within the cushion cavity, and wherein when the holder is in a container configuration, the combination of the holder and the base substantially encloses the containment volume defined by the base such that the sharps contact surface of the holder faces the containment volume when the holder is in the container configuration,
wherein one of the holder and the base comprises a track and the other of the holder and the base comprises a protrusion configured to be received within the track such that the protrusion is slidable within the track as the holder transitions from the stowed configuration toward the stand configuration.

24. The sharps handling device of claim 23, wherein the track defines a socket configured to receive the protrusion and to permit rotation of the protrusion therein.

25. The sharps handling device of claim 24, wherein the track comprises a biased arm configured to be displaced to permit the protrusion to enter the socket and configured to retain the protrusion within the socket.

26. The sharps handling device of claim 25, wherein the holder is configured to rotate relative to the base from the stand configuration into a container configuration in which the holder cooperates with the base to substantially enclose the containment volume.

27. The sharps handling device of claim 23, wherein the holder is configured to define a container configuration in which the holder cooperates with the base to substantially close the containment volume, and wherein the holder is configured to transition from the stowed configuration to the stand configuration while remaining coupled with the base and is configured to transition from the stand configuration to the container configuration while remaining coupled with the base.

28. The sharps handling device of claim 27, wherein the holder is configured to cooperate with the base to lock the holder in the container configuration.

* * * * *